(12) United States Patent
Tijanic et al.

(10) Patent No.: US 10,083,064 B2
(45) Date of Patent: *Sep. 25, 2018

(54) SYSTEMS AND METHODS FOR SMART TOOLS IN SEQUENCE PIPELINES

(71) Applicant: Seven Bridges Genomics Inc., Cambridge, MA (US)

(72) Inventors: Nebojsa Tijanic, Belgrade (RS); Luka Stojanovic, Belgrade (RS); Damir Cohadarevic, Belgrade (RS); Sinisa Ivkovic, Belgrade (RS)

(73) Assignee: Seven Bridges Genomics Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/381,492

(22) Filed: Dec. 16, 2016

(65) Prior Publication Data

US 2017/0199764 A1 Jul. 13, 2017

Related U.S. Application Data

(63) Continuation of application No. 14/877,378, filed on Oct. 7, 2015, now Pat. No. 9,558,321.

(Continued)

(51) Int. Cl.
*G06F 9/48* (2006.01)
*G06F 9/50* (2006.01)
*G06F 19/28* (2011.01)

(52) U.S. Cl.
CPC .......... *G06F 9/4881* (2013.01); *G06F 9/5005* (2013.01); *G06F 19/28* (2013.01)

(58) Field of Classification Search
None
See application file for complete search history.

(56) References Cited

U.S. PATENT DOCUMENTS 5,583,024 A 12/1996 McElroy et al.
5,674,713 A 10/1997 McElroy et al.
(Continued)

FOREIGN PATENT DOCUMENTS

KR 101282798 B1 7/2013
WO 2007086935 A3 8/2007
(Continued)

OTHER PUBLICATIONS

Abouelhoda, 2012, Tavaxy: integrating Taverna and Galaxy workflows with cloud computing support, BMC Bioinformatics 13:77.
(Continued)

*Primary Examiner* — Charles E Anya
*Assistant Examiner* — Timothy P Duncan
(74) *Attorney, Agent, or Firm* — Kip L. Bodi

(57) ABSTRACT

The invention relates to bioinformatics pipelines and wrapper scripts that call executables in those pipelines and that also identify beneficial changes to the pipelines. A tool in a pipeline has a smart wrapper that can cause the tool to analyze the sequence data it receives but that can also select a change to the pipeline when circumstances warrant. In certain aspects, the invention provides a system for genomic analysis. The system includes a processor coupled to a non-transitory memory. The system is operable to present to a user a plurality of genomic tools organized into a pipeline. At least a first one of the tools comprises an executable and a wrapper script. The system can receive instructions from the user and sequence data—instructions that call for the sequence data to be analyzed by the pipeline—and select, using the wrapper script, a change to the pipeline.

20 Claims, 15 Drawing Sheets

Related U.S. Application Data

(60) Provisional application No. 62/063,545, filed on Oct. 14, 2014.

(56) References Cited

U.S. PATENT DOCUMENTS

| | | | |
|---|---|---|---|
| 5,700,673 | A | 12/1997 | McElroy et al. |
| 5,701,256 | A | 12/1997 | Marr et al. |
| 6,210,891 | B1 | 4/2001 | Nyren et al. |
| 6,306,597 | B1 | 10/2001 | Macevicz |
| 6,818,395 | B1 | 11/2004 | Quake et al. |
| 6,828,100 | B1 | 12/2004 | Ronaghi |
| 6,833,246 | B2 | 12/2004 | Balasubramanian |
| 6,890,763 | B2 | 5/2005 | Jackowski et al. |
| 6,911,345 | B2 | 6/2005 | Quake et al. |
| 6,925,389 | B2 | 8/2005 | Hitt et al. |
| 6,989,100 | B2 | 1/2006 | Norton |
| 7,169,560 | B2 | 1/2007 | Lapidus et al. |
| 7,232,656 | B2 | 6/2007 | Balasubramanian et al. |
| 7,282,337 | B1 | 10/2007 | Harris |
| 7,598,035 | B2 | 10/2009 | Macevicz |
| 7,620,800 | B2 | 11/2009 | Huppenthal et al. |
| 7,835,871 | B2 | 11/2010 | Kain et al. |
| 7,917,302 | B2 | 3/2011 | Rognes |
| 7,960,120 | B2 | 6/2011 | Rigatti et al. |
| 8,146,099 | B2 | 3/2012 | Tkatch et al. |
| 8,209,130 | B1 | 6/2012 | Kennedy et al. |
| 8,370,079 | B2 | 2/2013 | Sorenson et al. |
| 9,063,914 | B2 | 6/2015 | Kural et al. |
| 9,116,866 | B2 | 8/2015 | Kural |
| 2002/0133504 | A1* | 9/2002 | Vlahos ............ G06F 17/30566 |
| 2002/0164629 | A1 | 11/2002 | Quake et al. |
| 2005/0282137 | A1 | 12/2005 | Sasinowski et al. |
| 2006/0024681 | A1 | 2/2006 | Smith et al. |
| 2006/0195269 | A1 | 8/2006 | Yeatman et al. |
| 2006/0292611 | A1 | 12/2006 | Berke et al. |
| 2007/0114362 | A1 | 5/2007 | Feng et al. |
| 2007/0166707 | A1 | 7/2007 | Schadt et al. |
| 2008/0251711 | A1 | 10/2008 | Reilly |
| 2008/0281463 | A1 | 11/2008 | Suh et al. |
| 2008/0294403 | A1 | 11/2008 | Zhu et al. |
| 2009/0026082 | A1 | 1/2009 | Rothberg et al. |
| 2009/0119313 | A1 | 5/2009 | Pearce |
| 2009/0127589 | A1 | 5/2009 | Rothberg et al. |
| 2009/0191565 | A1 | 7/2009 | Lapidus et al. |
| 2009/0300781 | A1 | 12/2009 | Bancroft et al. |
| 2010/0010992 | A1 | 1/2010 | Morris |
| 2010/0035252 | A1 | 2/2010 | Rothberg et al. |
| 2010/0137143 | A1 | 6/2010 | Rothberg et al. |
| 2010/0169026 | A1 | 7/2010 | Sorenson et al. |
| 2010/0188073 | A1 | 7/2010 | Rothberg et al. |
| 2010/0197507 | A1 | 8/2010 | Rothberg et al. |
| 2010/0282617 | A1 | 11/2010 | Rothberg et al. |
| 2010/0300559 | A1 | 12/2010 | Schultz et al. |
| 2010/0300895 | A1 | 12/2010 | Nobile et al. |
| 2010/0301398 | A1 | 12/2010 | Rothberg et al. |
| 2010/0304982 | A1 | 12/2010 | Hinz et al. |
| 2011/0009278 | A1 | 1/2011 | Kain et al. |
| 2011/0098193 | A1 | 4/2011 | Kingsmore et al. |
| 2011/0207135 | A1 | 8/2011 | Faham et al. |
| 2012/0030566 | A1 | 2/2012 | Victor |
| 2012/0040851 | A1 | 2/2012 | Lieberman et al. |
| 2012/0041727 | A1 | 2/2012 | Mishra et al. |
| 2012/0157322 | A1 | 6/2012 | Myllykangas et al. |
| 2012/0239706 | A1 | 9/2012 | Steinfadt |
| 2012/0330566 | A1 | 12/2012 | Chaisson |
| 2013/0029879 | A1 | 1/2013 | Shetty et al. |
| 2013/0035904 | A1 | 2/2013 | Kuhn |
| 2013/0059740 | A1 | 3/2013 | Drmanac et al. |
| 2013/0073214 | A1 | 3/2013 | Hyland et al. |
| 2013/0124100 | A1 | 5/2013 | Drmanac et al. |
| 2013/0232480 | A1 | 9/2013 | Winterfeldt et al. |
| 2013/0311106 | A1 | 11/2013 | White et al. |
| 2013/0345066 | A1 | 12/2013 | Brinza et al. |
| 2014/0051588 | A9 | 2/2014 | Drmanac et al. |
| 2014/0149725 | A1 | 5/2014 | Gherman et al. |
| 2014/0200147 | A1 | 7/2014 | Bartha et al. |
| 2014/0278590 | A1 | 9/2014 | Abbassi et al. |
| 2014/0280360 | A1 | 9/2014 | Webber et al. |
| 2014/0281708 | A1 | 9/2014 | Adam et al. |
| 2015/0020061 | A1 | 1/2015 | Ravi |
| 2015/0066383 | A1 | 3/2015 | Wernicke |

FOREIGN PATENT DOCUMENTS

| | | |
|---|---|---|
| WO | 2010010992 A1 | 1/2010 |
| WO | 2012098515 A1 | 7/2012 |
| WO | 2012142531 A2 | 10/2012 |
| WO | 2013035904 A1 | 3/2013 |

OTHER PUBLICATIONS

Agarwal, 2013, SINNET: Social Interaction Network Extractor from Text, Proc IJCNLP 33-36.

Aguiar, 2012, HapCompass: A fast cycle basis algorithm for accurate haplotype assembly of sequence data, J Comp Biol 19(6):577-590.

Airoldi, 2008, Mixed membership stochastic blockmodels, JMLR 9:1981-2014.

Altera, 2007, Implementation of the Smith-Waterman algorithm on reconfigurable supercomputing platform, White Paper ver 1.0 (18 pages).

Altschul, 1986, Optimal Sequence Alignment Using Affine Gap Costs, Bull Math Biol 48(5/6):603-616

Bansal, 2008, An MCMC algorithm for haplotype assembly from whole-genome sequence data, Genome Res 18:1336-1346.

Bao, 2013, BRANCH: boosting RNA-Seq assemblies with partial or related genomic sequences, Bioinformatics 29(10):1250-1259.

Bertone, 2004, Global identification of human transcribed sequences with genome tiling arrays, Science 306:2242-2246.

Bertrand, 2009, Genetic map refinement using a comparative genomic approach, J Comp Biol 16(10):1475-1486.

Black, 2005, A simple answer for a splicing conundrum, PNAS 102:4927-8.

Carrington, 1985, Polypeptide ligation occurs during post-translational modification of concanavalin A, Nature 313:64-67.

Chang, 2005, The application of alternative splicing graphs in quantitative analysis of alternative splicing form from EST database, Int J Comp Appl Tech 22(1):14.

Chen, 2012, Transient hypermutability, chromothripsis and replication-based mechanisms in the generation of concurrent clustered mutations, Mutation Res 750(1):562-59.

Chin, 2013, Nonhybrid finished microbial genome assemblies from long-read SMRT sequencing data, Nat Meth 10(6):563-569.

Chuang, 2001, Gene recognition based on DAG shortest paths, Bioinformatics 17(Suppl. 1):s56-s64.

Clark, 2014, Illumina announces landmark $1,000 human genome sequencing, Wired, Jan. 15, 2014.

Cock, 2013, Galaxy tools and workflows for sequence analysis with applications in molecular plant pathology, Peer J 1:e167.

Cohen-Boulakia, 2014, Distilling structure in Taverna scientific workflows: a refactoring approach, BMC Bioinformatics 15(Suppl 1):S12.

Compeau, 2011, How to apply de Bruijn graphs to genome assembly, Nat Biotech 29(11):987-991.

Costa, 2010, Uncovering the Complexity of Transcriptomes with RNA-Seq, J Biomed Biotech 853916.

Danecek, 2011, The variant call format and VCFtools, Bioinformatics 27(15):2156-2158.

Delcher, 1999, Alignment of whole genomes, Nucl. Acids Res 27(11):2369-76.

DePristo, 2011, A framework for variation discovery and genotyping using next-generation DNA sequencing data, Nat Gen 43:491-498.

Dinov, 2011, Applications of the pipeline environment for visual informatics and genomic computations, BMC Bioinformatics 12:304.

Dudley, 2009, A quick guide for developing effective bioinformatics programming skills, PLoS Comput Biol 5(12):e1000589.

(56) References Cited

OTHER PUBLICATIONS

Durham, 2005, EGene: a configurable pipeline system for automated sequence analysis, Bioinformatics 21(12):2812-2813.
Endelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Glusman, 2014, Whole-genome haplotyping approaches and genomic medicine, Genome Med 6:73.
Goto, 2010, BioRuby: bioinformatics software for the Ruby programming language, Bioinformatics 26(20):2617-2619.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Guttman, 2010, Ab initio reconstruction of cell type-specific transcriptomes of mouse reveals the concerved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harenberg, 2014, Community detection in large-scale networks: a survey and empirical evaluation, WIREs Comp Stat 6:426-439.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Hokamp, 2003, Wrapping up BLAST and Other Applications for Use on Unix Clusters, Bioinformatics 19(3)441-42.
Holland, 2008, BioJava: an open-source framework for bioinformatics, Bioinformatics 24(18):2096-2097.
Homer, 2010, Improved variant discovery through local re-alignment of short-read next generation sequencing data using SRMA, Genome Biol 11(10):R99.
Hoon, 2003, Biopipe: A flexible framework for protocol-based bioinformatics analysis, Genome Res 13(8):1904-1915.
Huang, Chapter 3: Bio-Sequence Comparison and Alignment, ser. Curr Top Comp Mol Biol. Cambridge, Mass.: The MIT Press, 2002.
Hull, 2006, Taverna: a tool for building and running workflows of services, Nucl Acids Res 34(Web Server issue): W729-32.
International HapMap Consortium, 2005, A haplotype map of the human genome. Nature 437:1299-1320.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014 (22 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
Kano, 2010, Text mining meets workflow: linking U-Compare with Taverna, Bioinformatics 26(19):2486-7.
Katoh, 2005, MAFFT version 5: improvement in accuracy of multiple sequence alignment, Nucl Acids Res 33(2):511-518.
Kawas, 2006, BioMoby extensions to the Taverna workflow management and enactment software, BMC Bioinformatics 7:523.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
Kumar, 2010, Comparing de novo assemblers for 454 transcriptome data, BMC Genomics 11:571.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Lanzen, 2008, The Taverna Interaction Service: enabling manual interaction in workflows, Bioinformatics 24(8):1118-20.
Larkin, 2007, Clustal W and Clustal X version 2.0, Bioinformatics 23(21):2947-2948.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.

(56) References Cited

OTHER PUBLICATIONS

Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, A survey of sequence alignment algorithms for next-generation sequencing, Briefings in Bionformatics 11(5):473-483.
Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6 (4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WIPO website of WO 2013/035904 (10 pages).
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
Miller, 2010, Assembly Algorithms for Next-Generation Sequencing Data, Genomics 95(6):315-327.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Driscoll et al. 'Big Data,' Hadoop and cloud computing in genomics, 2013, pp. 774-781, vol. 46, Journal of Biomedical Informatics.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation: Practice and Experience 18(10):1067-1100.
Oshlack, 2010, From RNA-seq reads to differential expression results. Genome Bio 11:220.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Pearson, 1988, Improved tools for biological sequence comparison, PNAS 85(8):2444-8.
Pe'er, 2006, Evaluating and improving power in whole-genome association studies using fixed marker sets. Nat Genet 38:663-667.
Peixoto, 2014, Efficient Monte Carlo and greedy heuristic for the inference of stochastic block models, Phys. Rev. E 89, 012804.
Posada, 1998, MODEL TEST: testing the model of DNA substitution, Bioinformatics 14(9):817-8.
Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Rajaram, 2013, Pearl millet [*Pennisetum glaucum* (L.) R. Br] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Rothberg, 2011, An integrated semiconductor device enabling non-optical genome sequencing, Nature 475:348-352.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schenk, 2013, A pipeline for comprehensive and automated processing of electron diffraction data in IPLT, J Struct Biol 182(2):173-185.
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.

(56) References Cited

OTHER PUBLICATIONS

Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5) 596-609.
Soni, 2007, Progress toward ultrafast DNA sequencing using solid-state nanopores, Clin Chem 53(11):1996-2001.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progressive approaches for segment-based multiple sequence alignment, Alg Mol Biol 3(1):1-11.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tan, 2010, A Comparison of Using Taverna and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
The Free Dictionary.com, Article about Client-server system originally from IGEL Technologies (2009) entitled: White Paper Cloud Computing: Thin clients in the cloud, Oct. 20, 2016 retrieval date; pp. 1-2.
The Free Dictionary.com, Article about Cloud computing originally from the Columbia Electronic Encyclopedia (2013) Oct. 20, 2016 retrieval date; Columbia Univ. Press—pp. 1-3.
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Truszkowski, 2011, New developments on the cheminformatics open workflow environment CDK-Taverna, J Cheminform 3:54.
Turi, 2007, Taverna Workflows: Syntax and Semantics, IEEE Int Conf on e-Science and Grid Computing 441-448.
Uchiyama et al., CGAT: a comparative genome analysis tool for visualizing alignments in the analysis of complex evolutionary changes between closely related genomes, 2006, e-pages 1-17, vol. 7:472; BMC Bioinformatics.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Wassink, 2009, Using R in Taverna: RShell v1.2. BMC Res Notes 2:138.
Waterman, 1976, Some biological sequence metrics, Adv Math 20(3):367-387.
Wellcome Trust Case Control Consortium, 2007, Genome-wide association study of 14,000 cases of seven common diseases and 3,000 shared controls, Nature 447:661-678.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Wu, 2010, Fast and SNP-tolerant detection of complex variants and splicing in short reads, Bioinformatics, 26(7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yang, 2014, Community detection in networks with node attributes, proc IEEE ICDM '13, arXiv:1401.7267.
Yanovsky, 2008, Read mapping algorithms for single molecule sequencing data, Proc 8th Int Workshop Alg Bioinformatics 5251:38-49.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Yu, 2010, The construction of a tetraploid cotton genome wide comprehensive reference map, Genomics 95:230-240.
Zhang, 2013, Taverna Mobile: Taverna workflows on Android, EMBnet J 19(B):43-45.
Zhao, 2012, Why Workflows Break-Understanding and Combating Decay in Taverna Workflows, eScience 2012, Chicago, Oct. 2012.

\* cited by examiner

SYSTEMS AND METHODS FOR SMART TOOLS IN SEQUENCE PIPELINES

CROSS-REFERENCE TO RELATED APPLICATION

This application is a continuation of U.S. patent application Ser. No. 14/877,378, filed Oct. 7, 2015, which application claims priority to, and the benefit of, U.S. Provisional Patent Application Ser. No. 62/063,545, filed Oct. 14, 2014, the contents of each of which are incorporated by reference.

FIELD OF THE INVENTION

The invention generally relates to bioinformatics pipelines and to wrapper scripts that call executables in those pipelines and that also identify beneficial changes to the pipelines.

BACKGROUND

Examining a person's genes can reveal if that person has a genetic disease or even if he or she is a latent carrier of a disease, at risk of passing the disease on to his or her children. The information is the persons' genes can be revealed by DNA sequencing. The DNA sequencing technologies known as next-generation sequencing (NGS) are capable of sequencing an entire human genome in under a day and for under $1,000. See Clark, Illumina announces landmark $1,000 human genome sequencing, Wired, 15 Jan. 2014. The output of NGS instruments typically includes many short sequence reads that must be assembled together and compared to known genetic information to meaningfully determine a person's genetic information.

This assembly and analysis is not a trivial task, and different computer program tools exist that perform various pieces of the assembly and analysis job. There are computer platforms that provide a graphical user interface (GUI) that can be used by a researcher or medical professional to assemble genomic analysis tools into pipelines that perform complex analytical tasks on sequence data. See, e.g., Toni, Next generation sequence analysis and computational genomics using graphical pipeline workflows, Genes (Basel) 3(3):545-75 (2012). However, these pipeline editors require the user to have mastered the intricacies of the underlying tools. If the user wants sequence reads to be aligned to a reference genome, for example, the user must be familiar with the myriad alignment tools such as MAQ, Burrows-Wheeler Aligner, SHRiMP, ZOOM, BFAST, MOSAIK, PERM, MUMmer, PROmer, BLAT, SOAP2, ELAND, RTG Investigator, Novoalign, Exonerate, Clustal Omega, ClustalW, ClustalX, and FASTA, to name a few. Additionally, the user must have a meaningful understanding of the sequence file (e.g., VCF, FASTA, FASTQ, SAM, GenBank, Nexus, EMBL, GCG, SwissProt, PR, phylip, msf, hennig86, jackknifer) and know which is which and at what points one needs to be converted to another, and what formats are the default inputs and outputs of each tool within a pipeline. Due to the complexities involved, working within a graphical pipeline editor does not solve all the challenges in assembling and analyzing sequence data. Data files may be passed along in the wrong format, causing a program to throw an error and abort the pipeline. In some cases, the tool selected to do a job will be a poor choice and will not work efficiently with the kind of data passed to it or—worse yet—will provide a substantively incorrect output. For example, an inconsistency between the choice of tool, the sequence data, the instructions provided by the user, and the user's expectation may actually cause the pipeline to not provide the correct result and potentially miss an important mutation.

SUMMARY

The invention provides pipelines in which a tool has a smart wrapper that can cause the tool to analyze the sequence data it receives but that can also select a change to the pipeline when circumstances warrant. For example, the smart wrapper can detect an inconsistency between the input data and the tool (e.g., wrong format) and can cause the pipeline to fix the input data before running the tool. Alternatively, the smart wrapper can detect an inconsistency between the input data and the tool and call an alternative second tool that accepts the input data format to perform the analysis. In another example, a smart wrapper can detect that a proposed analysis calls for some additional resource and can fetch that resource (e.g., can fetch a file containing a reference genome for variant calling). Smart wrappers can recover from pipeline errors by reading an error message and making the appropriate correction (e.g., a DNA sequence file that includes an "E" in the sequence data may cause a program to stop and issue an error; the smart wrapper could re-code the "E" to "N"). Since the smart wrapper is capable of dealing with errors from the tools or inconsistencies among the data, the tools, and the instructions, pipelines that include tools with smart wrappers will avoid mistakes and run to completion to provide the user with an analytical result that is correct and consistent with the user's expectations. Thus sequence assembly and analysis will produce the desired results and be successful, meaning that genetic sequence analysis can be adopted widely in medicine and research and used to solve scientific and medical problems.

In certain aspects, the invention provides a system for genomic analysis. The system includes a processor coupled to a non-transitory memory. The system is operable to present to a user a plurality of genomic tools organized into a pipeline. At least a first one of the tools comprises an executable and a wrapper script. The system can receive, from the user, instructions that call for the sequence data to be analyzed by the pipeline and sequence data and select, using the wrapper script, a change to the pipeline. The wrapper script may analyze the sequence data and select the change based on a feature of the sequence data. The change to the pipeline may include execution of an alternative executable instead of the executable. The wrapper script may select the change in response to an error produced by one of the tools. The wrapper script can recommend the change to the user and allows the user to accept the recommendation. In some embodiments, the wrapper script further performs the change to the pipeline.

In certain embodiments, the wrapper script selects to not analyze the sequence data with the executable. The wrapper script may recommend that the user use a second tool instead of the first one of the tools. For example, the executable may include a sequence alignment program and the change to the pipeline includes an alternative sequence alignment program.

The selected change may include a request for additional resources and the wrapper script can make the request. The requested additional resource may include using the system for: retrieving a data file not provided by the user and not included in the sequence data; retrieving data from a URL; retrieving a matrix of probabilities; calling for a first tool in the pipeline to generate ancillary data from the sequence data to be used by a subsequent tool in the pipeline when the subsequent tool analyzes the sequence data; requesting additional computing power; requesting additional computer processors; requesting one or more virtual machines; and requesting additional storage space.

The instructions may include at least one flag that establishes a value for a parameter, and the smart wrapper selects the change by changing the flag to establish a different value for the parameter. The wrapper script can add a flag to the instructions that sends a parameter to the executable, wherein the parameter controls how the executable analyzes the sequence data.

In some embodiments, the wrapper script selects the change to the pipeline by receiving an error from the executable, making an adjustment that avoids the error and re-running the executable.

The wrapper script can be used to detect an inconsistency between the instructions and the executable, between the instructions and the sequence data, or between the sequence data and the executable. The wrapper script may cause the system to: prompt the user for additional data; prompt the user to accept the selected change; inform the user of the selected change; or take other action.

Aspects of the invention provide a method for genomic analysis. The method includes using a computer system comprising a processor coupled to a memory subsystem for presenting to a user a plurality of genomic tools organized into a pipeline (wherein at least a first one of the tools comprises an executable and a wrapper script), receiving instructions from the user and sequence data, wherein the instructions call for the sequence data to be analyzed by the pipeline, and selecting—using the wrapper script—a change to the pipeline. In some embodiments, the change to the pipeline comprises execution of an alternative executable instead of the executable. Optionally, the wrapper script further performs the change to the pipeline.

In certain embodiments, the wrapper script selects the change in response to an error produced by the first one of the tools. The wrapper script may recommend the change to the user and allows the user to accept the recommendation. The executable may include a sequence alignment program and the change to the pipeline may include an alternative sequence alignment program.

In certain embodiments the selected change includes a request for additional resources and the wrapper script makes the request (e.g., retrieving a data file not provided by the user and not included in the sequence data; retrieving data from a URL; retrieving a matrix of probabilities; calling for a first tool in the pipeline to generate ancillary data from the sequence data to be used by a subsequent tool in the pipeline when the subsequent tool analyzes the sequence data; requesting additional computing power; requesting additional computer processors; requesting one or more virtual machines; or requesting additional storage space).

In some embodiments, the wrapper script selects the change to the pipeline by receiving an error from the executable, making an adjustment that avoids the error, and re-running the executable.

In certain embodiments, the instructions include at least one flag that establishes a value for a parameter, and the smart wrapper selects the change by changing the flag to establish a different value for the parameter. The wrapper script may select a change that comprises not analyzing the sequence data with the executable. The wrapper script may detect an inconsistency, e.g., between the instructions and the executable, between the instructions and the sequence data, or between the sequence data and the executable. Selecting the change may include recommending that the user use a second tool instead of the first one of the tools. In some embodiments, the wrapper script adds a flag to the instructions that sends a parameter to the executable, wherein the parameter controls how the executable analyzes the sequence data. The wrapper script may cause the system to: prompt the user for additional data, prompt the user to accept the selected change, inform the user of the selected change, or combinations thereof. In some embodiments, the wrapper script analyzes the sequence data and selects the change based on a feature of the sequence data.

DETAILED DESCRIPTION

Figure 1:
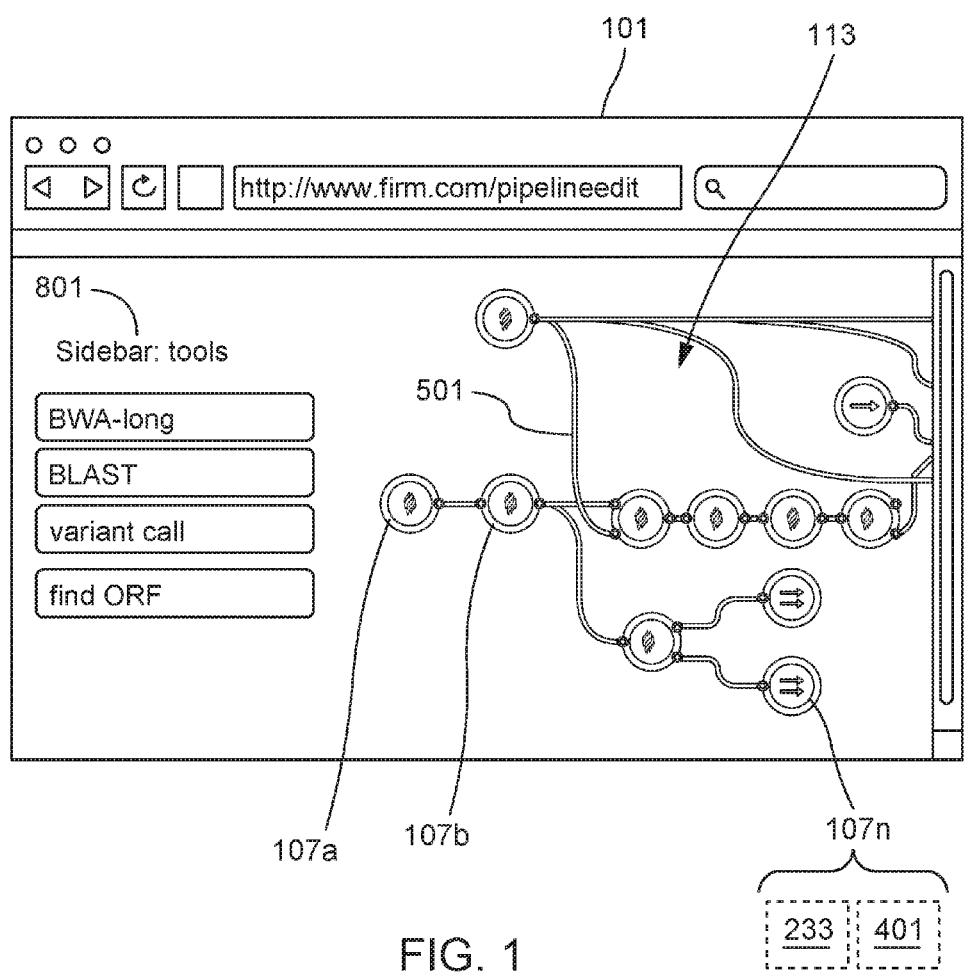
FIG. 1 illustrates a pipeline editor.

FIG. 1 illustrates a pipeline editor 101 according to some embodiments. Pipeline editor 101 may be presented in any suitable format such as a dedicated computer application or as a web site accessible via a web browser. Generally, pipeline editor 101 will present a work area in which a user can see and access icons representing a plurality of tools 107a, 107b, . . . , 107n. Tools may be dragged from sidebar 801 into the workspace of editor 101 and connected to one another by connectors 501. Any tool 107n may include a wrapper script 233n and a binary executable 401n. In certain embodiments, executable 401n will be a sequence analysis executable. Wrapper script 233 evaluates and reacts to parameters or inputs given to tool 107, any input data, the associated executable 401n, the environment in which tool 107 is running, or errors generated by executable 401n. A novel feature of the invention is that a wrapper script 233 can identify, suggest, or implement a change to pipeline 113. A change may be, to illustrate, running an alternative executable 401m instead of executable 401n as caused by wrapper script 233n.

Tool 107 may be represented within pipeline editor 101 as an icon. In general, a tool 107 will have at least one input or output that can be linked to one or more input or output of another tool 107. The inputs and outputs of the tools can be represented graphically as little symbols (nodules) attached to the icon. A set of linked tools may be referred to as a pipeline. The graphical user interface of pipeline editor 101 allows a user to link pairs of the executables via their respective output and input streams to define a pipeline.

Figure 5:
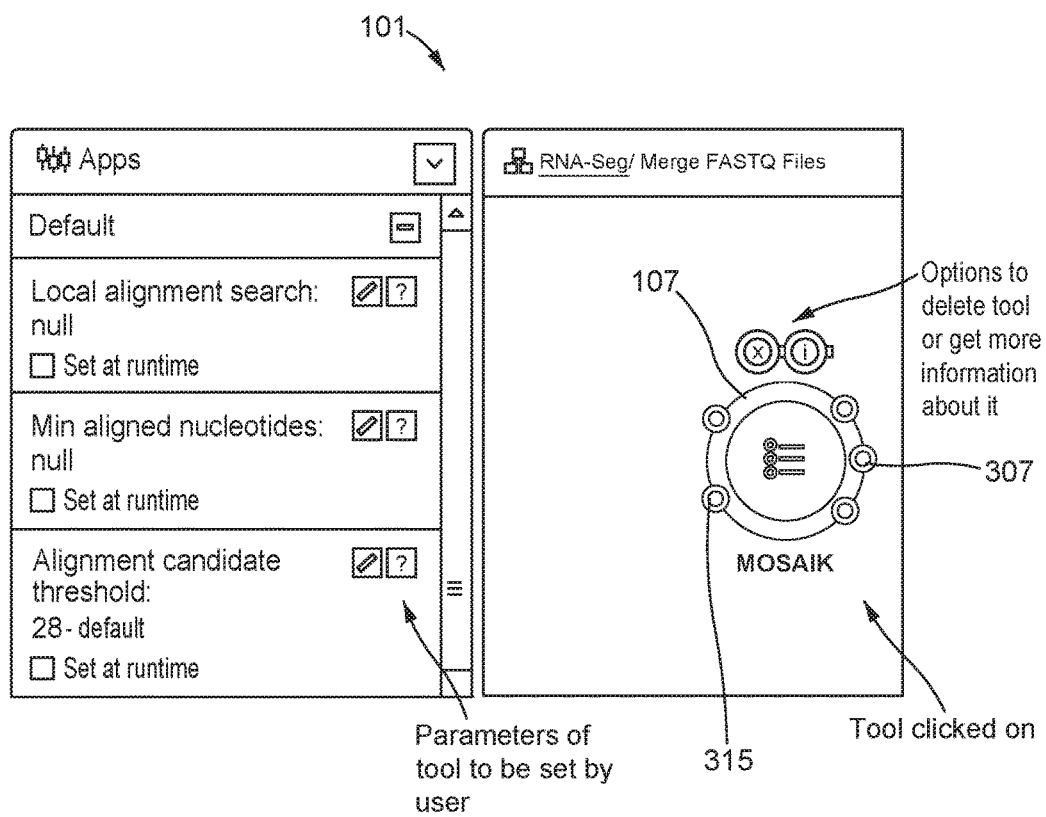
FIG. 5 gives a display presented by pipeline editor.

Selecting (e.g., clicking on) a tool allows parameters of that tool to be set (see FIG. 5). The parameters are then passed on during execution by the wrappers (see, e.g., FIG. 10). A pipeline 113 can be built by connecting combinations of the tools with connectors 501 that represent data-flows from one tool to another. FIGS. 11-14 illustrate a variety of sample pipelines in which the files that serve as the pipeline's inputs and outputs may be represented as nodes, just like tools. Input files are connected via connectors to the input nodules on the tools they serve as inputs for, and output files are connected to the output nodules on the tools that generate them. Input and output nodes can represent single files, or they can represent multidimensional data structures such as a list of files, a list of lists of files, others, or a combination thereof.

In some embodiments, input and output files consist of sequence data and associated meta-data, including file type (.bam, .fastq, etc.) along with other properties such as sample id, date created, author, others, or a combination thereof. Preferably, input file types and dimensions will match that required by the tool being fed. Where a tool 107 includes a sequence analysis executable, the sequence analysis executable will generally define an input stream and an output stream (represented as input and output points, respectively, of corresponding tool 107).

Figure 2:
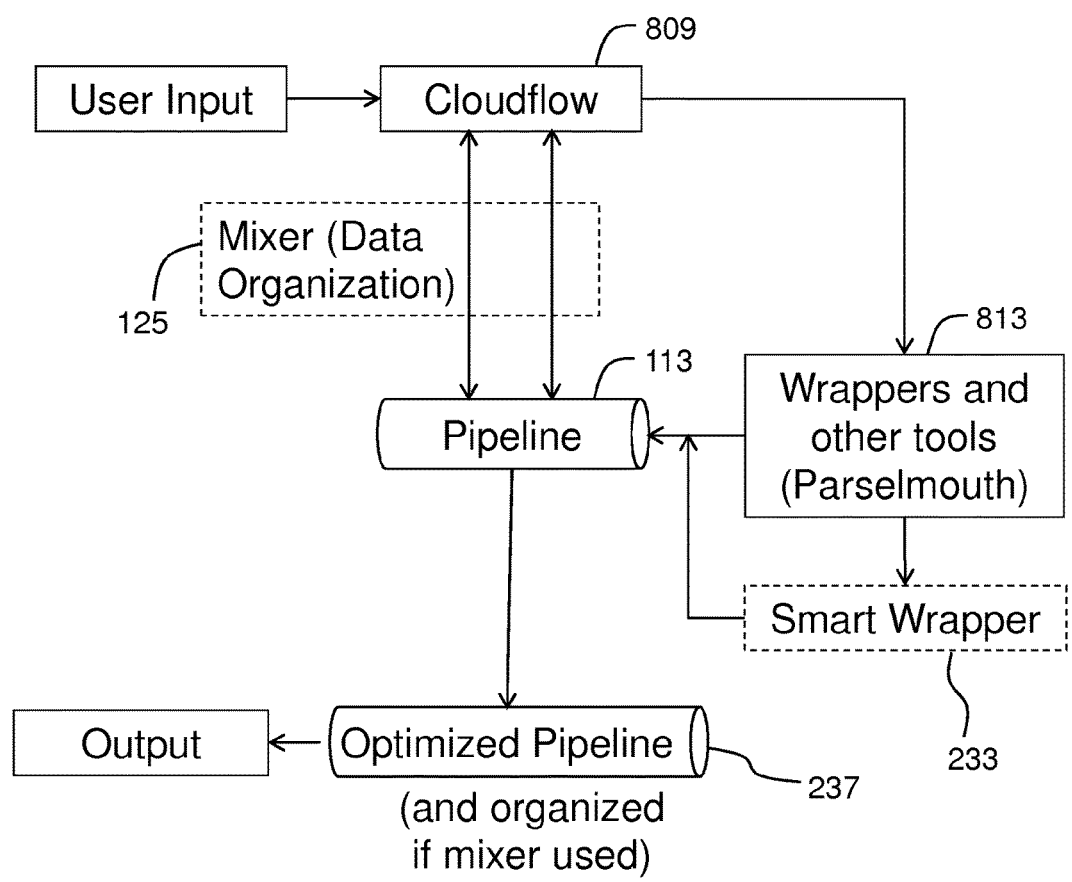
FIG. 2 presents an overview of a workflow involving a pipeline.

FIG. 2 presents an overview of a workflow involving a pipeline 113 according to a certain implementation of the invention. Pipeline module 809 is a system component that runs pipelines 113. Pipeline module 809 executes a tool 107 by running wrapper script 233 (which may be provided by scripts—such as Python scripts). Wrapper script 233 calls executable 401, sets the parameters and inputs (in accord with either what the user has selected, what previous tools in the pipeline have generated, what the execution environment requires, or sensible defaults), sets the output file paths, runs executable 401 and passes along any errors thrown.

Wrapper script 233 does more than just run tool executable 401 and return the tool's outputs or errors. Wrapper script 233 can suggest that pipeline module 809 do something other than what is strictly indicated by the design of pipeline 113, the input data, or the user's instructions to get a desired result.

In some embodiments, pipeline module 809 will follow the suggestions from wrapper script 233 automatically by default, but if the wrapper script 233 includes a "prompt" job, then pipeline module 809 will instead pass along the suggestion to the user for a decision on whether or not to follow the suggestion (this is important in cases where the suggestion from wrapper script 233 may alter the results obtained). In some cases, the wrapper script 233 may include a "notify" job instead, which would signal to pipeline module 809 to go ahead and follow the suggestion but send a heads up message to the user informing them of the change.

Wrapper script 233 can log or record the suggestions and any changes made to the optimized pipeline 237 run as a result of those suggestions or changes from wrapper script 233, to ensure reproducibility, allow for debugging, inform users, and other such functionality. Wrapper script 233 can perform a variety of functions including such broad categories of functions as proposing an alternative job, requesting additional resources, and recovering from errors intelligently.

One important category of functions provided by a wrapper script 233 includes proposing an alternative job. A wrapper script 233 can evaluate the parameters and inputs it has been given and suggest to pipeline module 809 that a different set of parameters and inputs or even running a different tool would be better for getting the desired result (see FIG. 10).

Instead of returning outputs or an error, wrapper script 233 essentially returns "run THIS instead", where THIS fully describes the alternate job including tools, parameters, and inputs.

Reasons why wrapper script 233 might propose an alternative job include: (i) some combination of input data, tools 107, and user instructions and parameters will result in an error; (ii) an alternate set of input data, tools 107, and user instructions and parameters might run more efficiently, saving the user time or money (e.g., where the user pays for execution costs); (iii) the parameters and inputs given strongly suggest a user error, and therefore running the job as ordered would be a waste (this would call for the "notify" job); and (iv) an alternate set of input data, tools 107, and user instructions and parameters will give a 'better' result from a scientific standpoint (e.g., a more accurate alignment) without significant tradeoffs (this would be a good place for the "prompt" job, since the user should make the ultimate call on substantive scientific questions).

The alternative job proposed by wrapper script 233 can actually be a set of jobs. For example, wrapper script 233 may suggest that the system "run this (some other) pipeline", or "run this tool and then take its outputs and feed it into this next tool", or "run these tools (or several instances of the same tool) in parallel".

One important category of functions provided by a wrapper script 233 includes requesting additional resources. A wrapper script 233 can also evaluate the resources a tool 107 has available to it on the machine (e.g., Amazon EC2 instance) that the tool 107 is running on, and tell pipeline module 809 that tool 107 needs additional resources to do the job. Resources requested might include elements of the execution environment, such as extra computing power or memory. Resources requested might also include particular files/data, specified by URL, which are then saved in a cache to ensure reproducibility even if the version at the URL changes.

Just as proposing an alternative job can include proposing an alternative set of jobs, requesting an additionally resource can be a multi-step process. For example, wrapper script 233 may issue an instruction that says, in essence, "go to the database at URL X, enter this SQL query, and provide me with the output."

One important category of functions provided by a wrapper script 233 includes recovering from errors intelligently. While some of the wrapper script 233 functions described here take place before the tool is run, wrapper script 233 can also evaluate errors thrown by a tool and suggest an alternative that would avoid the error. The suggested alternatives can take the form of different parameters/tools/inputs or additional resources.

In some embodiments, pipeline module 809 requests AWS Elastic Cloud Compute (EC2) instances (e.g., to provide command module 819 in FIG. 10) for running tools from tool module 813, the component which abstracts EC2 service and keeps a "pool" of available instances. Pipeline module 809 decides what sort of instance is needed based on wrapper metadata, which contains information on the resources (CPU, memory, storage) a tool requires, sometimes including specific resource requests for particular sub-jobs. In the depicted implementation, pipeline module 809 causes a tool module 813 to execute individual tools 401. User input (e.g., in the form of sequence files) is run through pipeline 113, with wrapper 233 reading inputs, instructions, metadata, and executables and controlling the flow of sequence data through pipeline 113. Since a wrapper 233 can actually cause substantive changes to pipeline 113 (e.g., cause executable 401b to run instead of 401a), it can be thought of that wrapper 233 provides an organized optimized pipeline 237, which provides the output.

Generally, a smart wrapper 233 is included in a tool 107 along with a sequence analysis executable 401. When a pipeline 113 calls tool 107n, the wrapper script 233n of that tool 107n calls executable 401n. Sequence analysis executables can include, for example, GATK, Paup*, MrBayes, etc. Any such executable 401n may be a compiled, executable binary (e.g., accessible at/bin). The corresponding wrapper script 233n generally includes a command to execute executable 401n and may include information to manage input or output data, settings flags, error codes, logging, running a program in the background, or other such functionality that will be appreciated by one of skill in the art. A wrapper script may be created in any suitable language known in the art including, for example, bash, Perl, Python, or others. FIG. 2 illustrates that a smart wrapper 233 can be understood as contributing an optimized pipeline 237 from a pipeline 113.

As discussed above, a pipeline generally refers to a bioinformatics workflow that includes one or a plurality of individual steps. Each step (embodied and represented as a tool 107 within pipeline editor 101) generally includes an analysis or process to be performed on genetic data. For example, an analytical project may begin by obtaining a plurality of sequence reads. The pipeline editor 101 can provide the tools to quality control the reads and then to assemble the reads into contigs. The contigs may then be compared to a references, such as the human genome (e.g., hg18) to detect mutations by a third tool. These three tools—quality control, assembly, and compare to reference—as used on the raw sequence reads represent but one of myriad genomic pipelines. Genomic pipelines are discussed in Dinov, 2011, Applications of the pipeline environment for visual informatics and genomic computations, BMC Bioinf 12:304 and Torri, 2012, Next generation sequence analysis and computational genomics using graphical pipeline workflows, Genes (Basel) 3:545, the contents of each of which are incorporated by reference.

As represented in FIG. 1, each step is provided as a tool 107. Any tool 107 may perform any suitable analysis such as, for example, alignment, variant calling, RNA splice modeling, quality control, data processing (e.g., of FASTQ, BAM/SAM, or VCF files), or other formatting or conversion utilities. Pipeline editor 101 represents tools 107 as "apps" and allows a user to assemble tools into a pipeline 113.

Small pipelines can be included that use but a single app, or tool. For example, editor 101 can include a merge FASTQ pipeline that can be re-used in any context to merge FASTQ files. Complex pipelines that include multiple interactions among multiple tools (e.g., such as a pipeline to call variants from single samples using BWA+GATK) can be created to store and reproduce published analyses so that later researchers can replicate the analyses on their own data. Using the pipeline editor 101, a user can browse stored tools and pipelines to find a stored tool 107 of interest that offers desired functionality. The user can then copy the tool 107 of interest into a project, then run it as-is or modify it to suit the project. Additionally, the user can build new analyses from scratch.

Embodiments of the invention can include server computer systems that provide pipeline editor 101 as well as computing resources for performing the analyses represented by pipeline 113. Computing execution and storage can be provided by one or more server computers of the system, by an affiliated cloud resource, by a user's local computer resources, or a combination thereof.

Figure 3:
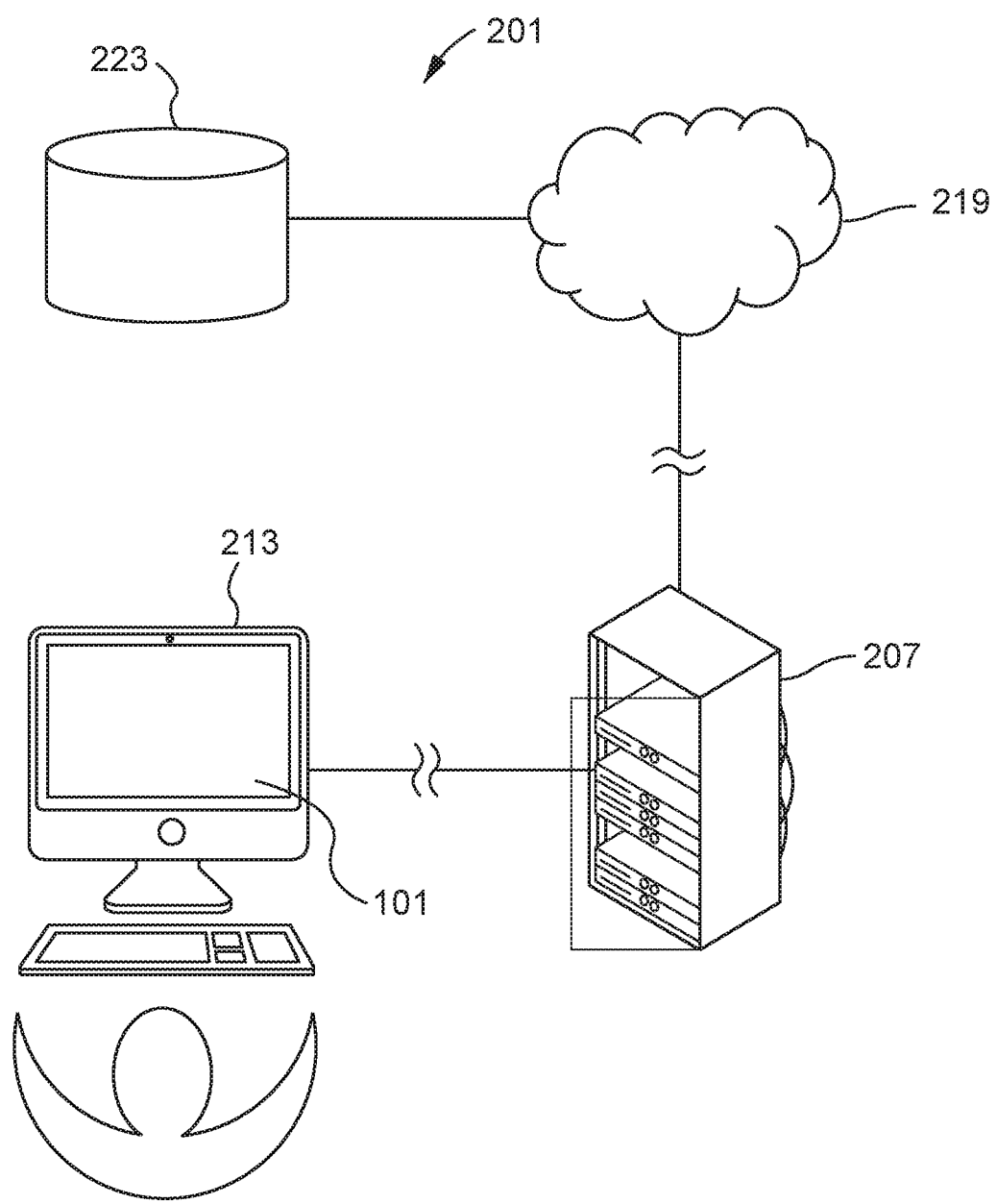
FIG. 3 diagrams a system according to certain embodiments.

FIG. 3 diagrams a system 201 according to certain embodiments. System 201 generally includes a server computer system 207 to provide functionality such as access to one or more tools 107. A user can access pipeline editor 101 and tools 107 through the use of a local computer 213. A pipeline module on server 207 can invoke the series of tools 107 called by a pipeline 113. A tool module can then invoke the commands or program code called by the tool 107. Commands or program code can be executed by processing resources of server 207. In certain embodiments, processing is provided by an affiliated cloud computing resource 219. Additionally, affiliated storage 223 may be used to store data.

A user can interaction with pipeline editor 101 through a local computer 213. Local computer 213 can be a laptop, desktop, or mobile device such as a tablet or smartphone. In general, local computer 213 is a computer device that includes a memory coupled to a processor with one or more input/output mechanism. Local computer 213 communicates with server 207, which is generally a computer that includes a memory coupled to a processor with one or more input/output mechanism. These computing devices can optionally communicate with affiliated resource 219 or affiliated storage 223, each of which preferably use and include at least computer comprising a memory coupled to a processor.

As one skilled in the art would recognize as necessary or best-suited for performance of the methods of the invention, systems of the invention include one or more computer devices that include one or more processors (e.g., a central processing unit (CPU), a graphics processing unit (GPU), etc.), computer-readable storage devices (e.g., main memory, static memory, etc.), or combinations thereof which communicate with each other via a bus. A computer generally includes at least one processor coupled to a memory via a bus and input or output devices.

A processor may be any suitable processor known in the art, such as the processor sold under the trademark XEON E7 by Intel (Santa Clara, Calif.) or the processor sold under the trademark OPTERON 6200 by AMD (Sunnyvale, Calif.).

Memory preferably includes at least one tangible, non-transitory medium capable of storing: one or more sets of instructions executable to cause the system to perform functions described herein (e.g., software embodying any methodology or function found herein); data (e.g., embodying any tangible physical objects such as the genetic sequences found in a patient's chromosomes); or both. While the computer-readable storage device can in an exemplary embodiment be a single medium, the term "computer-readable storage device" should be taken to include a single medium or multiple media (e.g., a centralized or distributed database, and/or associated caches and servers) that store the instructions or data. The term "computer-readable storage device" shall accordingly be taken to include, without limit, solid-state memories (e.g., subscriber identity module (SIM)

card, secure digital card (SD card), micro SD card, or solid-state drive (SSD)), optical and magnetic media, and any other tangible storage media.

Any suitable services can be used for affiliated resource 219 or affiliated storage 223 such as, for example, Amazon Web Services. In some embodiments, affiliated storage 223 is provided by Amazon Elastic Block Store (Amazon EBS) snapshots, allowing cloud resource 219 to dynamically mount Amazon EBS volumes with the data needed to run pipeline 113. Use of cloud storage 223 allows researchers to analyze data sets that are massive or data sets in which the size of the data set varies greatly and unpredictably. Thus, systems of the invention can be used to analyze, for example, hundreds of whole human genomes at once.

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

As shown in FIG. 1, within pipeline editor 101, individual tools (e.g., command line tools) are represented as an icon in a graphical editor.

Figure 4:
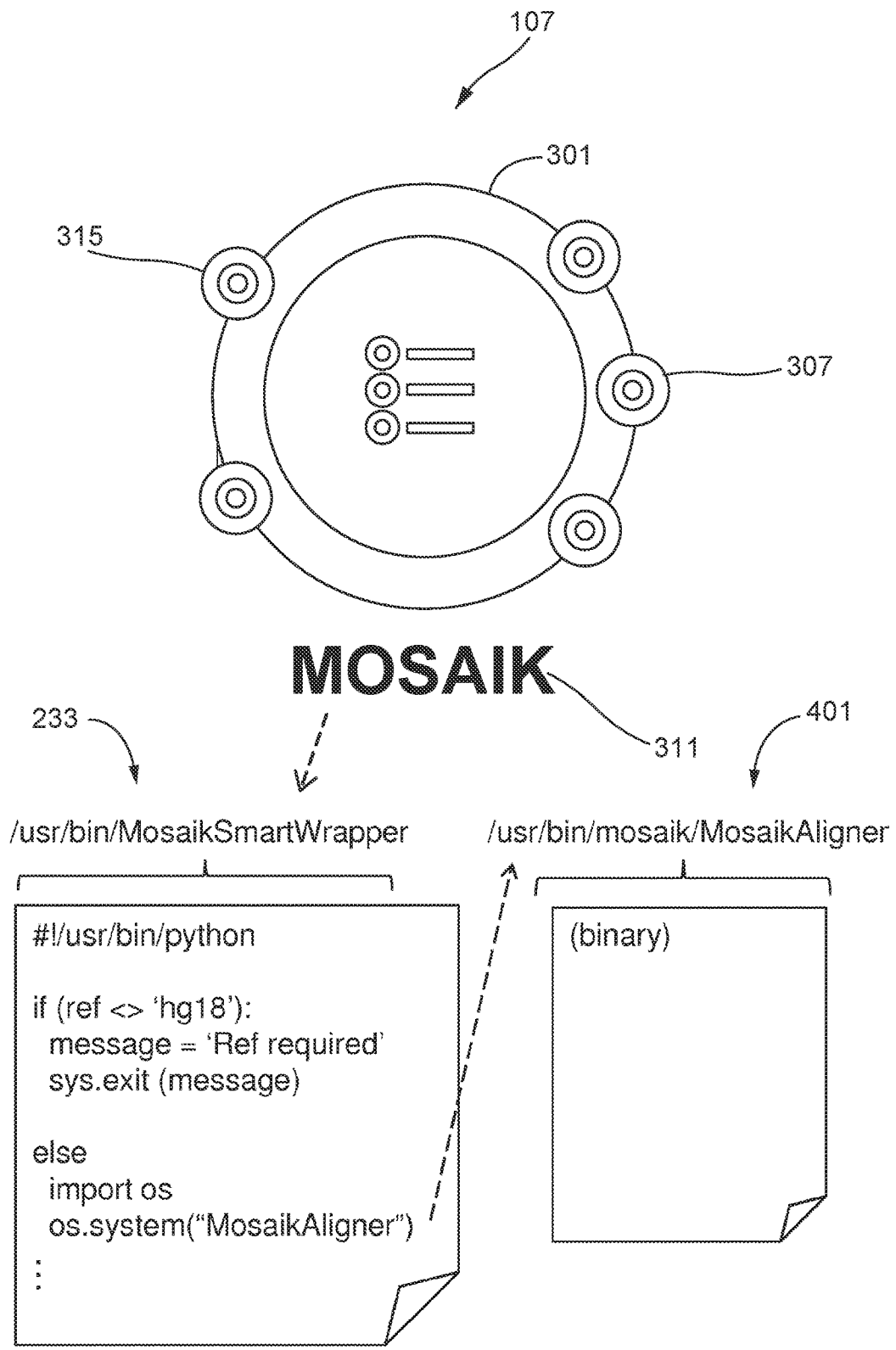
FIG. 4 depicts a tool that includes a wrapper script.

FIG. 4 depicts a tool 107, shown represented as an icon 301. Tool 107 includes wrapper script 233, which has the ability to call executable 401. Icon 301 may have one or more output point 307 and one or more input point 315 corresponding to output and input pipes, respectively, of executable 401. In embodiments in which a tool 107 includes an underlying sequence analysis executable, input point 315 is analogous to an argument or data that can be piped in and output point 307 represents the output of the command. Icon 301 may be displayed with a label 311 to aid in recognizing tool 107. In some embodiments, selecting, or single-clicking on, the icon 301 for tool 107 allows parameters of the tool to be set within pipeline editor 101.

When a pipeline 113 that includes tool 107 is run, at the point during the pipeline workflow where tool 107 is to be called, pipeline module 809 will call wrapper script 233. In the illustrative embodiment shown in FIG. 4, script 233 is a Python script that checks first to see if the variable ref has been assigned the contents of file hg18 (here shown in a simplified pseudo-code for illustrative purposes). If hg18 has not been assigned to ref, script 233 exits and tells the user that a reference is required. In the illustrated example, executable 401 is Mosaik aligner, which aligns reads to a reference. A user has set up wrapper script 233 to require hg18 as the reference that Mosaik will use. The user has thus used wrapper script 233 to interrupt the running of pipeline 113 in the event, for example, that the reference is set to hg19. If ref has been set to hg18, then wrapper 233 issues the system command MosaikAligner which causes executable 401 to run. Script 233 can pass along the switches or flags as well as the data to Mosaik. This described functionality is accessible via pipeline editor 101.

FIG. 5 gives a display presented by pipeline editor 101 when a tool 107 is selected. The tool may include buttons for deleting that tool or getting more information associated with the icon 301. Additionally, a list of parameters for running the tool may be displayed with elements such as tick-boxes or input prompts for setting the parameters (e.g., analogous to switches or flags in UNIX/LINUX commands). Clicking on tool 107 allows parameters of the tool to be set within editor 101 (e.g., within a GI). As discussed in more detail below, the parameter settings will then be passed through the tool module to the command-level module. A user may build pipeline 113 by placing connectors between input points 315 and output points 307.

Figure 6:
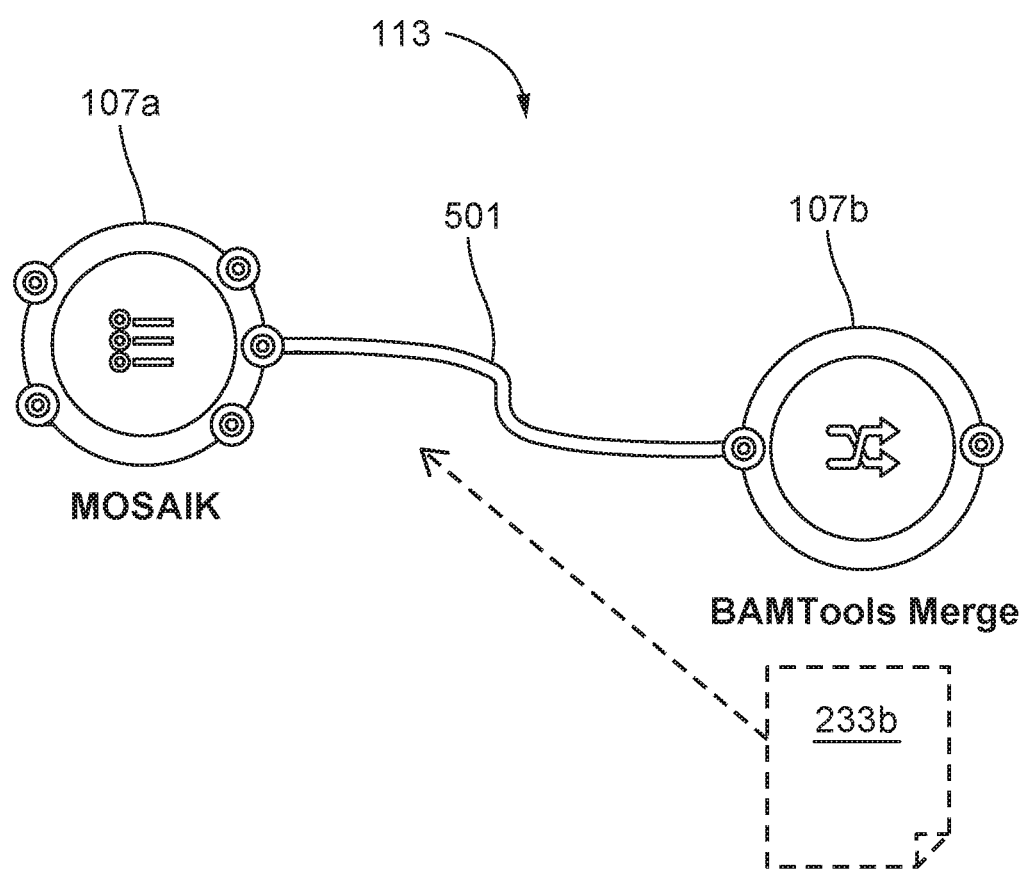
FIG. 6 illustrates a wrapper of a tool.

FIG. 6 illustrates how a wrapper 233b sits beneath a tool 107b within a pipeline 113. Here, pipeline 133 includes a connector 501 connecting a first tool 107a to a second tool 107b. Connector 501 represents a data-flow from first tool 107a to second tool 107b (e.g., analogous to the pipe (|) character in UNIX/LINUX text commands). Wrapper 233b evaluates the output of tool 107a, instructions and flags (i.e., switches or parameters) from a user, an executable associated with tool 107b, and can respond to any inconsistency among those. For example, the command "bamtools merge" may be invoked by wrapper 233b to call bamtools merge as executable 401b. Wrapper 233b expects the output of tool 107a to thus be numerous small BAM files. In a given instance, a user may be running a job that will cause tool 107a to output only a single BAM file. In this instance, wrapper 233b may detect that inconsistence between the input to tool 107b and the corresponding executable 401b, and may be pre-programmed to, under those facts, simply skip tool 107b without further comment (or optionally to give a notification).

Figure 7:
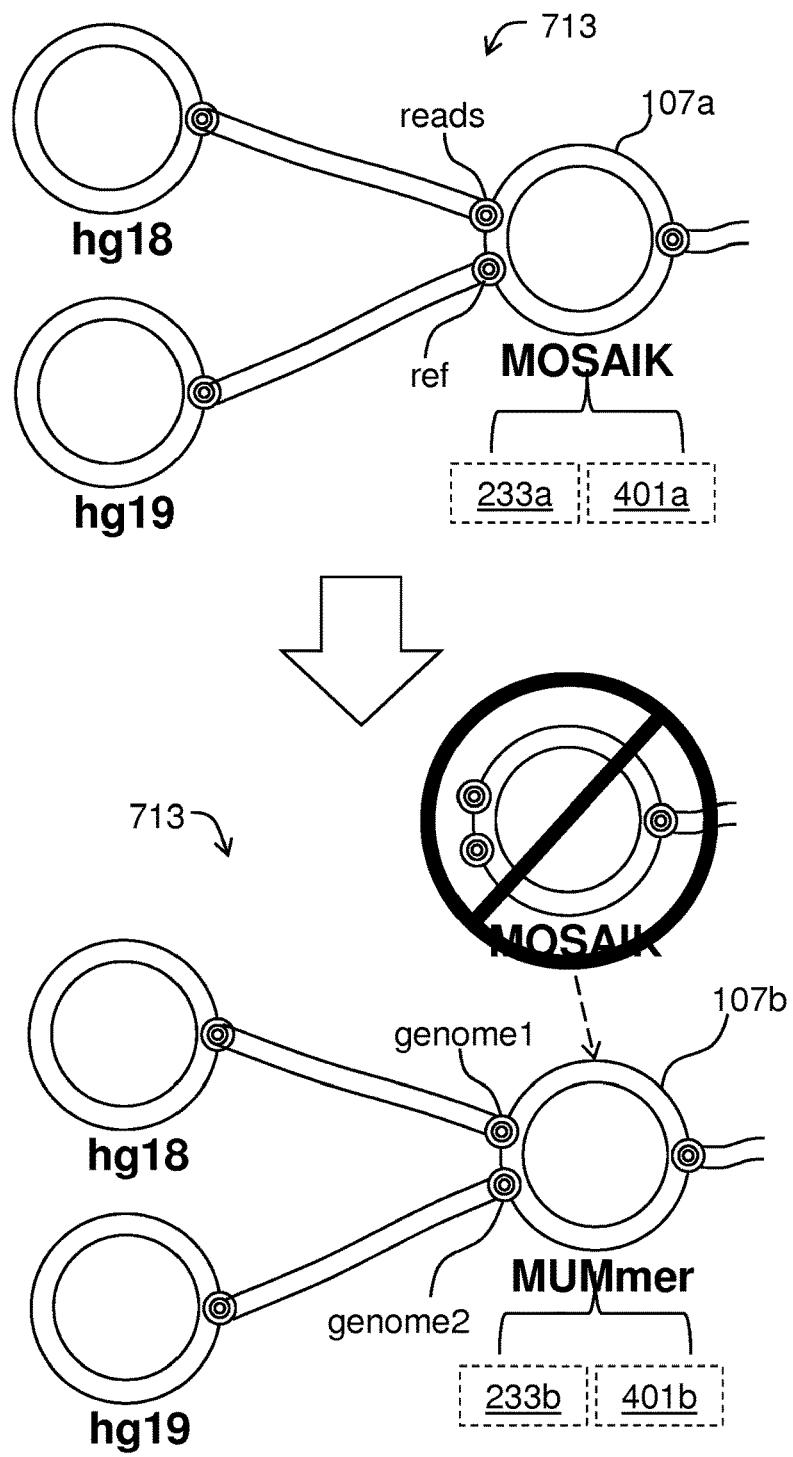
FIG. 7 shows a graphical representation of using a smart wrapper.

FIG. 7 shows a graphical representation of using a smart wrapper 233 to keep an analysis running even where there is an inconsistency between a user's instructions and the input data. Here, pipeline 713 includes Mosaik as tool 107a, and a user has set up pipeline to align hg18 to hg19. Wrapper script 233a detects that the user's instructions to align hg18 to hg19 are not consistent with the use of Mosaik, which expects to align numerous short reads to a reference. Script 233a identifies that pipeline 713 can be changed to include MUMmer instead of Mosaik. This can be accomplished by any suitable means. For example, script 233a can include a table or a series of "if . . . elseif . . . " statements that assign input to specific aligners based on qualities of the input. The qualities of the input that script 233a examines include, for example, file size, extension, file format, number of input files, metadata, or other information. In the illustrate example, script 233a may recognize that a set of files with a *.vcf extension and one genome-sized file are suitable for Mosaik. However, script 233a may recognize that two files of substantially equal size are not suited to being aligned by Mosaik and are suited to be aligned by MUMmer. See, e.g., Delcher, et al., 1999, Alignment of whole genomes, Nucleic Acids Research 27(11):2369-2376. Script 233a identifies that pipeline 713 should be updated so that it would execute MUMmer as executable 401b. In some embodiments, script 233a will simply make that change, and MUMmer will align hg18 to hg19. It is worth noting that the updated pipeline 713 will call MUMmer as tool 107b, and that this may call script 233b.

Figure 8:
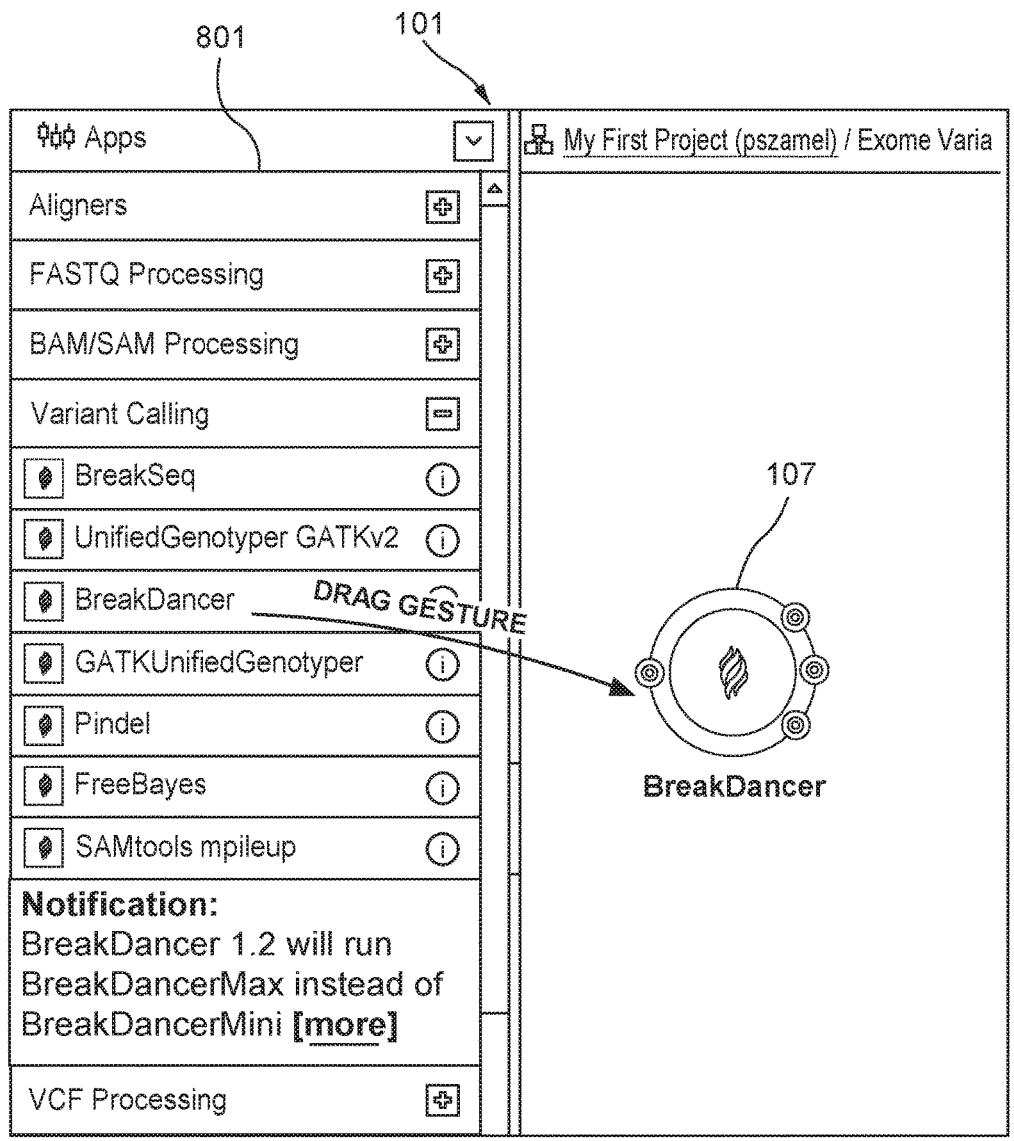
FIG. 8 illustrates how a tool may be brought into pipeline editor.

FIG. 8 illustrates how a tool 107 may be brought into pipeline editor 101 for use within the editor. In some embodiments, pipeline editor 101 includes an "apps list" 801 shown in FIG. 8 as a column to the left of the workspace in which available tools are listed. In some embodiments, apps on apps list 801 can be dragged out into the workspace where they will appear as icons. A user can perform a drag gesture to bring any tool (i.e., any App) into the workspace of pipeline editor 101.

Systems described herein may be embodied in a client/server architecture. Alternatively, functionality described herein may be provided by a computer program application that runs solely on a client computer (i.e., runs locally). A client computer can be a laptop or desktop computer, a portable device such as a tablet or smartphone, or specialized computing hardware such as is associated with a sequencing instrument. For example, in some embodiments, functions described herein are provided by an analytical unit of an NGS sequencing system, accessing a database according to embodiments of the invention and assembling sequence reads from NGS and reporting results through the terminal hardware (e.g., monitor, keyboard, and mouse) connected directly to the NGS system. In some embodiments, this functionality is provided as a "plug-in" or functional component of sequence assembly and reporting software such as, for example, the GS De Novo Assembler, known as gsAssembler or Newbler (NEW assemBLER) from 454 Life Sciences, a Roche Company (Branford, Conn.). Newbler is designed to assemble reads from sequencing systems such as the GS FLX+ from 454 Life Sciences (described, e.g., in Kumar, S. et al., Genomics 11:571 (2010) and Margulies, et al., Nature 437:376-380 (2005)). In some embodiments, a production application is provided as functionality within a sequence analyzing system such as the HiSeq 2500/1500 system or the Genome AnalyzerIIX system sold by Illumina, Inc. (San Diego, Calif.) (for example, as downloadable content, an upgrade, or a software component).

Figure 9:
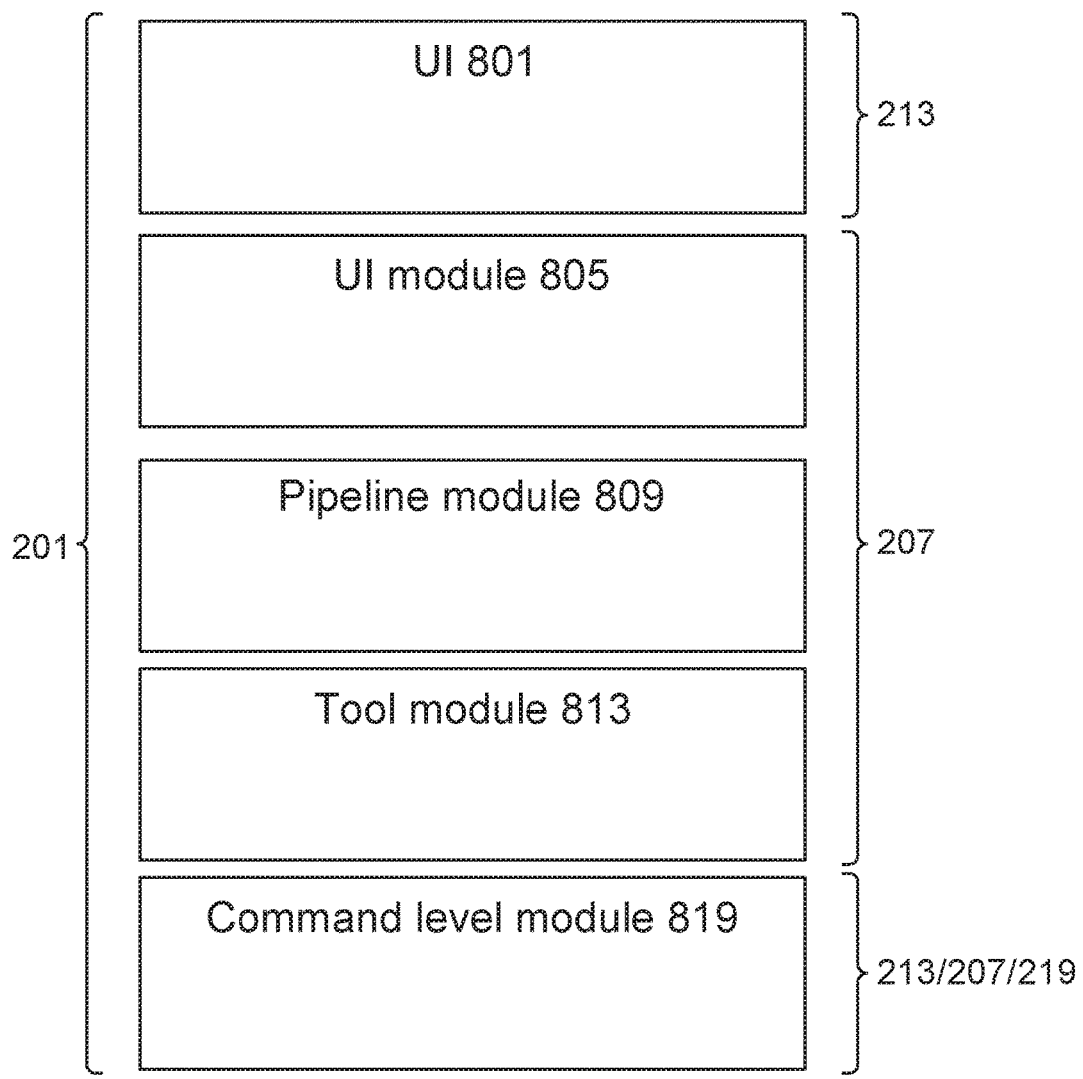
FIG. 9 illustrates functional components of a system of the invention.

FIG. 9 illustrates functional components of a system 201 according to certain embodiments. Generally, a user will interact with a user interface (UI) 801 provided within, for example, local computer 213. A UI module 805 may operate within server system 207 to send instructions to and receive input from UI 801. Within server system 207, UI module 805 sits on top of pipeline module 809 which executes pipelines 113. Pipeline module 809 executes wrapper scripts 233. Pipeline module 809 directly handles scheduling and execution of tasks, while an independent component may be employed to allocated instances and make sure they're being used efficiently. The running, or execution, of tools 107 is done by the wrapper scripts 233 (see FIG. 10 for more detail).

Preferably, UI module 801, pipeline module 809, and tool module 813 are provided at least in part by server system 207. In some embodiments, affiliated cloud computing resource 219 contributes the functionality of one or more of UI module 801, pipeline module 809, and tool module 813. Command-level module 819 may be provided by one or more of local computer 213, server system 207, cloud computing resource 219, or a combination thereof. It is noted that as drawn in FIG. 10, the ">" character does not represent the info line prefix of a FASTA file but instead here represents a UNIX prompt to show that command module 819 hypothetically receives the commands for tools p, q, r, x, y, and z to be executed with output piped to input along the chain.

Computer program instructions can be written using any suitable language known in the art including, for example, Perl, BioPerl, Python, C++, C#, JavaScript, Ruby on Rails, Groovy and Grails, or others. Program code can be linear, object-oriented, or a combination thereof. Preferably, program instructions for the tools described here are provided as distinct modules, each with a defined functionality. Exemplary languages, systems, and development environments include Perl, C++, Python, Ruby on Rails, JAVA, Groovy, Grails, Visual Basic .NET. An overview of resources useful in the invention is presented in Barnes (Ed.), Bioinformatics for Geneticists: A Bioinformatics Primer for the Analysis of Genetic Data, Wiley, Chichester, West Sussex, England (2007) and Dudley and Butte, A quick guide for developing effective bioinformatics programming skills, PLoS Comput Biol 5(12):e1000589 (2009).

In some embodiments, systems of the invention are developed in Perl (e.g., optionally using BioPerl). Perl is discussed in Tisdall, Mastering Perl for Bioinformatics, O'Reilly & Associates, Inc., Sebastopol, Calif. 2003. In some embodiments, tools 107 are developed using BioPerl, a collection of Perl modules that allows for object-oriented development of bioinformatics applications. BioPerl is available for download from the website of the Comprehensive Perl Archive Network (CPAN). See also Dwyer, Genomic Perl, Cambridge University Press (2003) and Zak, CGI/Perl, 1st Edition, Thomson Learning (2002).

In certain embodiments, systems of the invention are developed using Java and optionally the BioJava collection of objects, developed at EBI/Sanger in 1998 by Matthew Pocock and Thomas Down. BioJava provides an application programming interface (API) and is discussed in Holland, et al., BioJava: an open-source framework for bioinformatics, Bioinformatics 24(18):2096-2097 (2008). Java is discussed in Liang, Introduction to Java Programming, Comprehensive (8th Edition), Prentice Hall, Upper Saddle River, N.J. (2011) and in Poo, et al., Object-Oriented Programming and Java, Springer Singapore, Singapore, 322 p. (2008).

Systems of the invention can be developed using the Ruby programming language and optionally BioRuby, Ruby on Rails, or a combination thereof. Ruby or BioRuby can be implemented in Linux, Mac OS X, and Windows as well as, with JRuby, on the Java Virtual Machine, and supports object oriented development. See Metz, Practical Object-Oriented Design in Ruby: An Agile Primer, Addison-Wesley (2012) and Goto, et al., BioRuby: bioinformatics software for the Ruby programming language, Bioinformatics 26(20): 2617-2619 (2010).

Systems and methods of the invention can be developed using the Groovy programming language and the web development framework Grails. Grails is an open source model-view-controller (MVC) web framework and development platform that provides domain classes that carry application data for display by the view. Grails domain classes can generate the underlying database schema. Grails provides a development platform for applications including web applications, as well as a database and an object relational mapping framework called Grails Object Relational Mapping (GORM). The GORM can map objects to relational databases and represent relationships between those objects. GORM relies on the Hibernate object-relational persistence framework to map complex domain classes to relational database tables. Grails further includes the Jetty web container and server and a web page layout framework (SiteMesh) to create web components. Groovy and Grails are discussed in Judd, et al., Beginning Groovy and Grails, Apress, Berkeley, Calif., 414 p. (2008); Brown, The Definitive Guide to Grails, Apress, Berkeley, Calif., 618 p. (2009).

Figure 10:
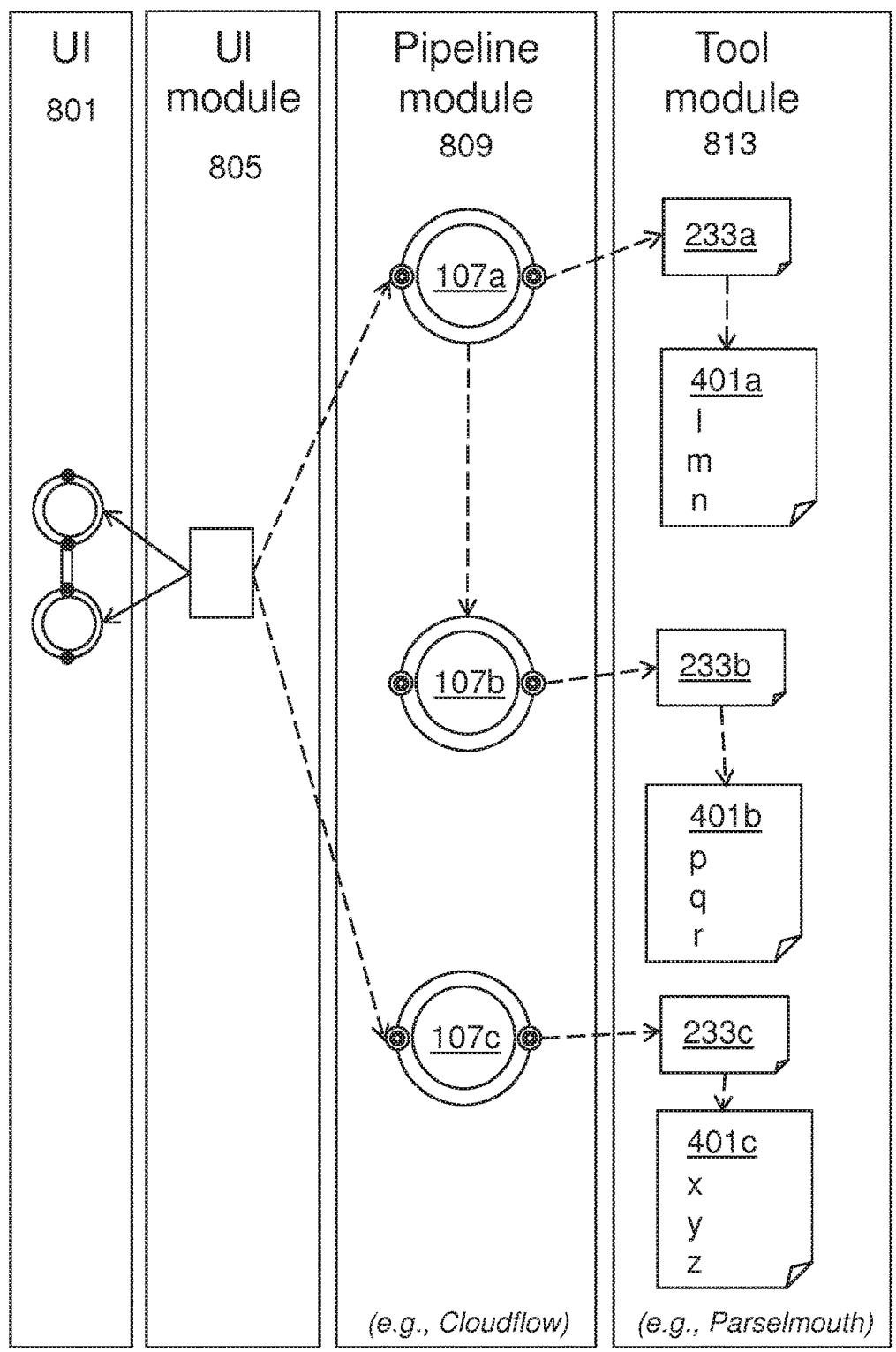
FIG. 10 illustrates the operation of systems of the invention.

FIG. 10 illustrates the operation and inter-relation of components of systems of the invention. In certain embodiments, a pipeline 113 is stored within pipeline module 809. Pipeline 113 may be represented using any suitable language or format known in the art. In some embodiments, a pipeline is described and stored using JavaScript Object Notation (JSON). The pipeline JSON objects include a section describing nodes (nodes include tools 107 as well as input points 315 and output points 307) and a section describing the relations (i.e., connections 501) between the nodes.

Pipeline module 809 actually executes wrapper scripts 233 and may also be the component that executes these pipelines 113. Running or executing the wrapper scripts 233 is what runs or executes the tools 107.

Tool module 813 manages information about the wrapped tools 107 that make up pipelines 113 (such as inputs/outputs and resource requirements). Tool module 813 stores the wrappers 233. The executables 401 may themselves comprise one or any number of commands (e.g., l, m, n, . . . or p, q, r, . . . or x, y, z . . . , to illustrate).

The UI module 805 handles the front-end user interface. This module can represent workflows from pipeline module 809 graphically as pipelines in the graphical pipeline editor 101. The UI module can also represent the tools 107 that make up the nodes in each pipeline 113 as node icons 301 in the graphical editor 101, generating input points 315 and output points 307 and tool parameters from the information in tool module 813. The UI module will list other tools 107 in the "Apps" list along the side of the editor 101, from whence the tools 107 can be dragged and dropped into the pipeline editing space as node icons 301.

In certain embodiments, UI module 805, in addition to listing tools 107 in the "Apps" list, will also list other pipelines the user has access to (separated into "Public Pipelines" and "Your Custom Pipelines"), getting this information from pipeline module 809.

Using systems described herein, a wide variety of genomic analytical pipelines may be provided. In general, pipelines will relate to analyzing genetic sequence data. The variety of pipelines that can be created is open-ended and unlimited. In some embodiments, one or more pipelines may be included in system 201 as a tool for use in pipeline editor 101. For example, certain genomic analytical steps may be routine and common and thus conducive to be being offered as a pre-made pipeline.

To illustrate the breadth of possible analyses that can be supported using system 201 and to introduce a few exemplary pipelines that may be included for use within a system of the invention, a few example pipelines are discussed.

Figure 11:
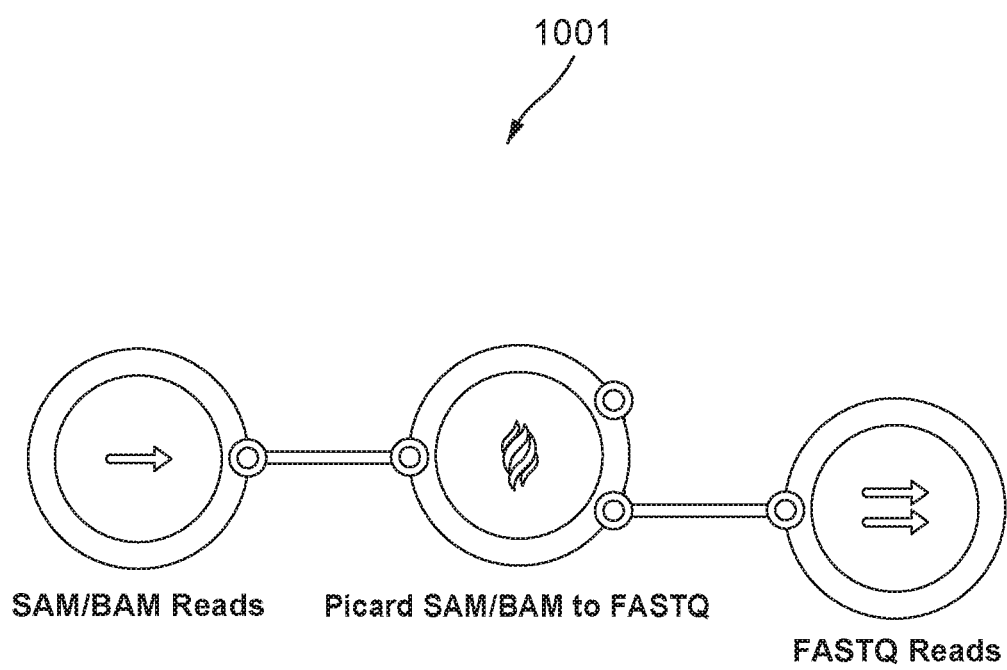
FIG. 11 illustrates a pipeline that converts a SAM file into a FASTQ file.

FIG. 11 illustrates a relatively simple pipeline 1001 that converts a sequence alignment map (SAM) file or a binary version of a SAM (BAM) into a FASTQ file.

Figure 12:
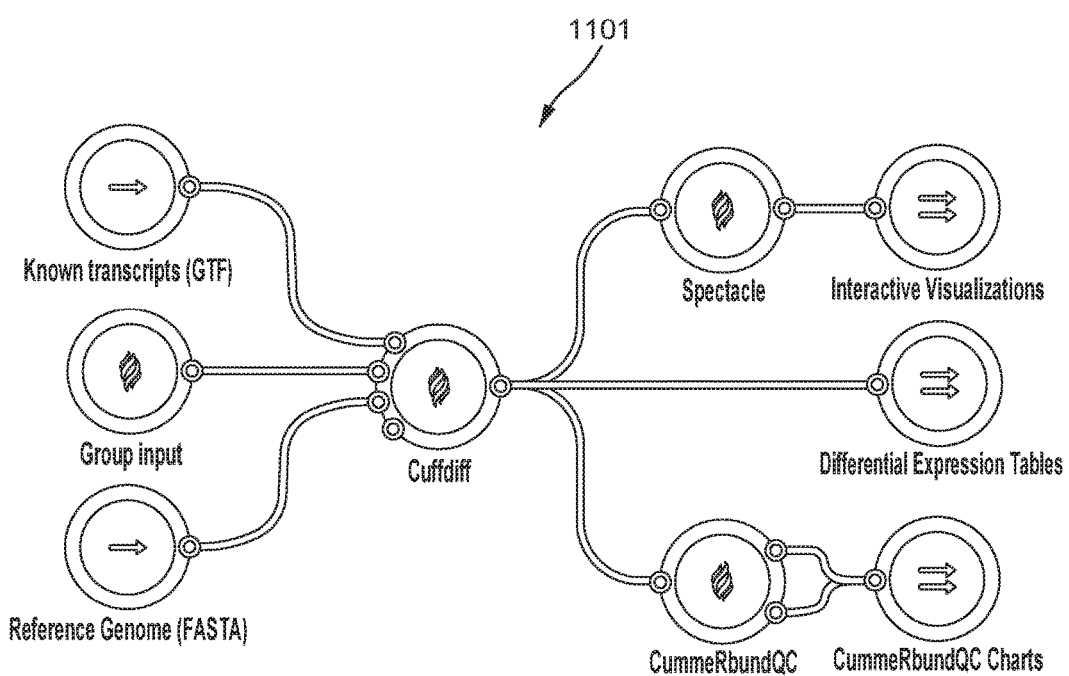
FIG. 12 shows a pipeline for differential expression analysis.

FIG. 12 shows a pipeline 1101 for differential expression analysis using the program Cuffdiff. Pipeline 1101 can find significant differences in transcript expression between groups of samples. In pipeline 1101, Cuffdiff accepts read alignment files from any number of groups containing one or more samples, it calculates expression levels at the isoform and gene level, and it tests for significant expression differences. Cuffdiff outputs a downloadable collection of files, viewable as spreadsheets that can be explored. This pipeline can also perform basic quality control of differential expression experiment powered by CummeRbund. Lastly, pipeline 1101 can render interactive visualizations from Cuffdiff results. This allows a user to explore differential expression results in the form of interactive plots, export gene sets, and generate publication quality figures.

Another analysis included in a system of the invention can provide an alignment summary.

Figure 13:
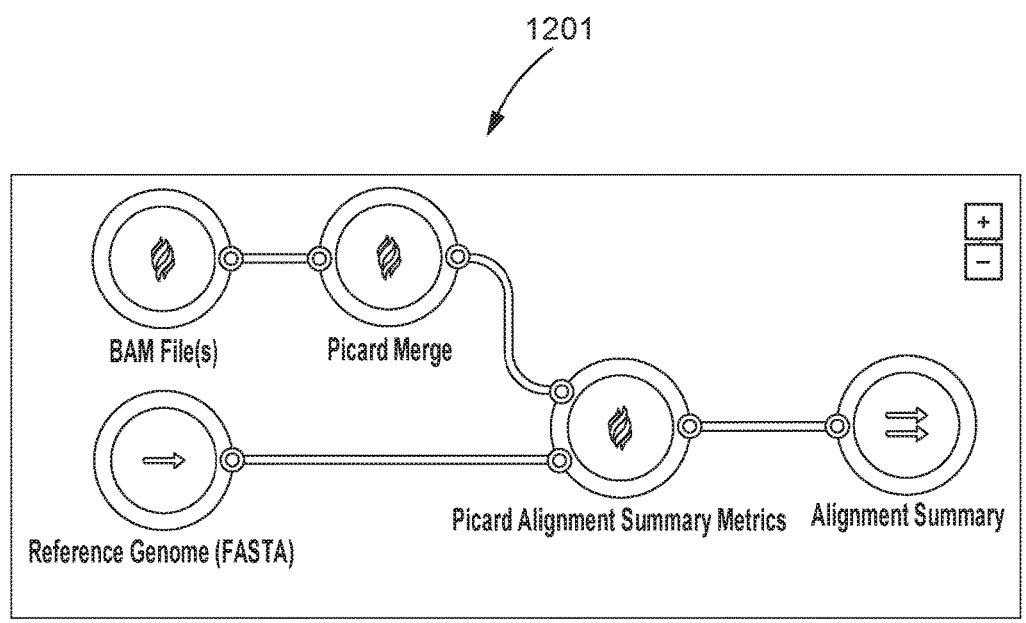
FIG. 13 shows a pipeline for providing an alignment summary.

FIG. 13 shows a pipeline 1201 for providing an alignment summary. Pipeline 1201 can be used to analyze the quality of read alignment for both genomic and transcriptomic experiments. Pipeline 1201 gives useful statistics to help judge the quality of an alignment. Pipeline 1201 takes aligned reads in BAM format and a reference FASTA to which they were aligned as input, and provides a report with information such as the proportion of reads that could not be aligned and the percentage of reads that passed quality checks.

Figure 14:
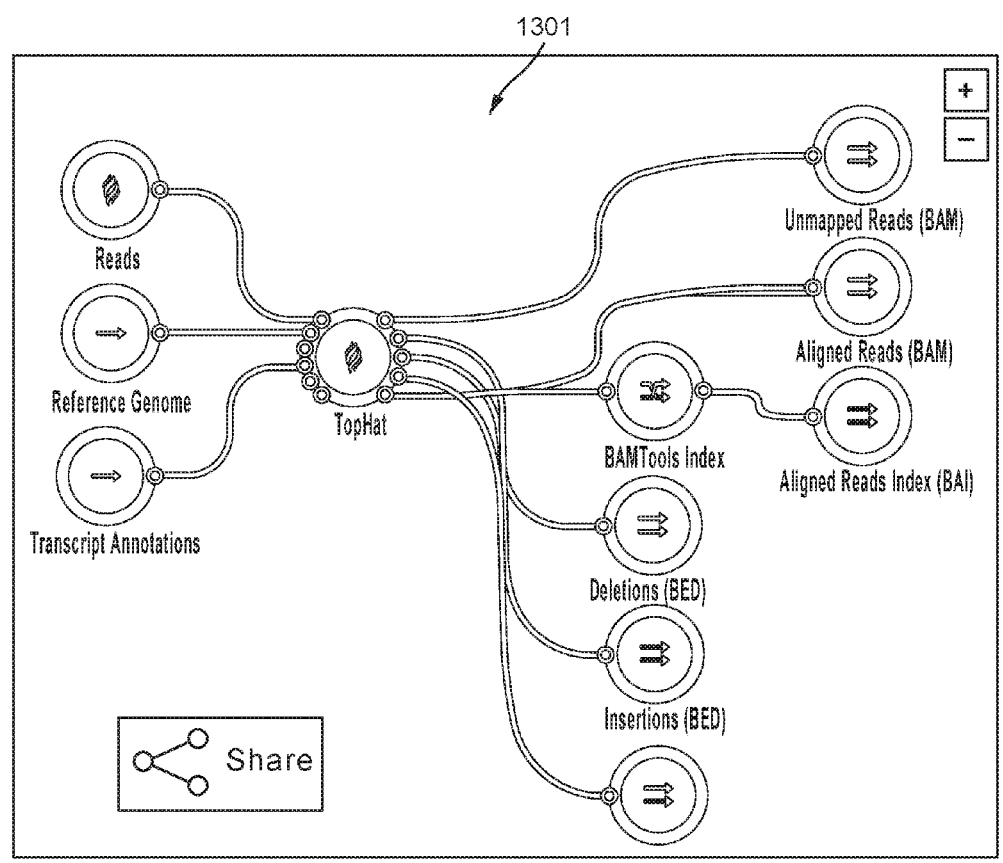
FIG. 14 depicts a pipeline for split read alignment.
Figure 15:
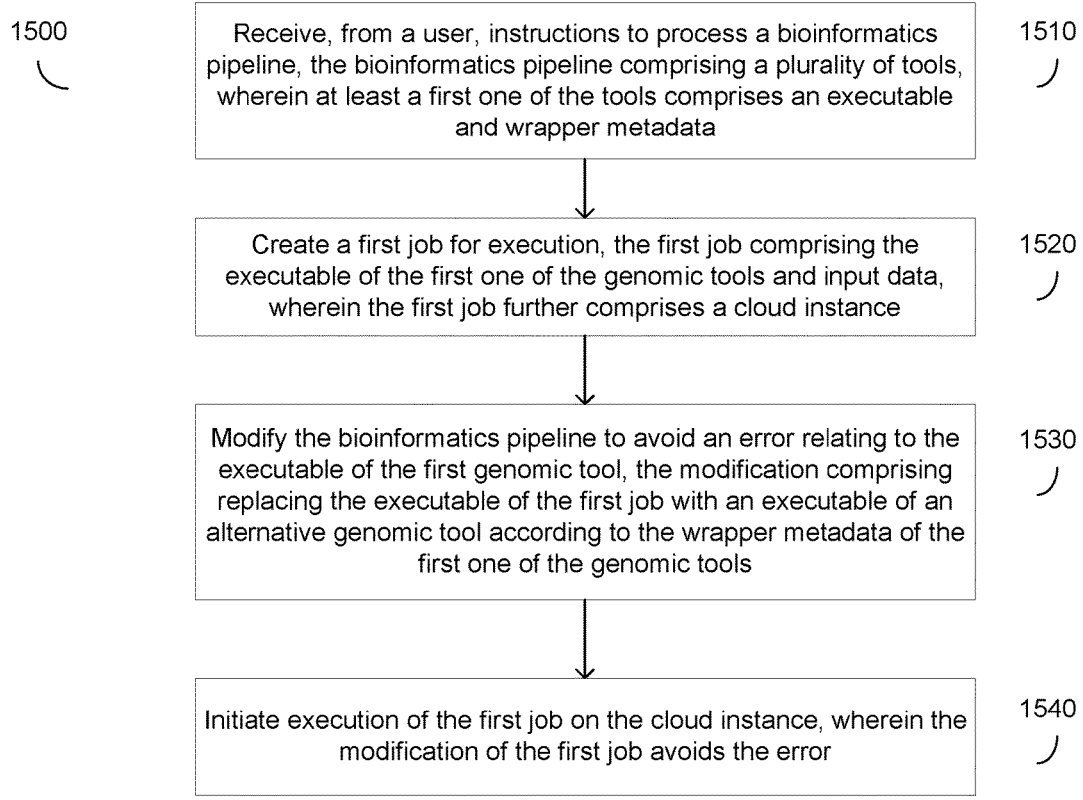
FIG. 15 is a flow diagram depicting an embodiment of a method for processing a bioinformatics pipeline.
Figure 16:
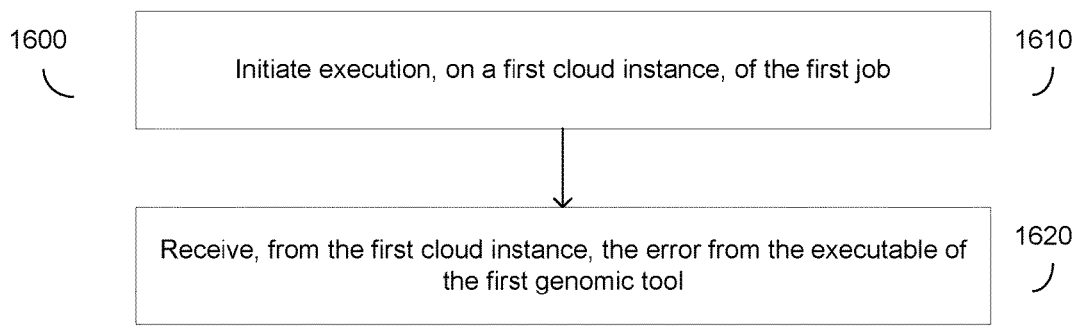
FIG. 16 is a flow diagram depicting an embodiment of a method of creating a first job for execution.

FIG. 14 depicts a pipeline 1301 for split read alignment. Pipeline 1301 uses the TopHat aligner to map sequence reads to a reference transcriptome and identify novel splice junctions. The TopHat aligner is discussed in Trapnell, et al., TopHat: discovering splice junctions with RNA-Seq. Bioinformatics 2009, 25:1105-1111, incorporated by reference. Pipeline 1301 accommodates the most common experimental designs. The TopHat tool is highly versatile and the pipeline editor 101 allows a researcher to build pipelines to exploit its many functions.

Other possible pipelines can be created or included with systems of the invention. For example, a pipeline can be provided for exome variant calling using BWA and GATK.

An exome variant calling pipeline using BWA and GATK can be used for analyzing data from exome sequencing experiments. It replicates the default bioinformatics pipeline used by the Broad Institute and the 1000 Genomes Project. GATK is discussed in McKenna, et al., 2010, The Genome Analysis Toolkit: a MapReduce framework for analyzing next-generation DNA sequencing data, Genome Res. 20:1297-303 and in DePristo, et al., 2011, A framework for variation discovery and genotyping using next-generation DNA sequencing data, Nature Genetics. 43:491-498, the contents of both of which are incorporated by reference. The exome variant calling pipeline can be used to align sequence read files to a reference genome and identify single nucleotide polymorphisms (SNPs) and short insertions and deletions (indels).

Other pipelines that can be included in systems of the invention illustrate the range and versatility of genomic analysis that can be performed using system 201. System 201 can include pipelines that: assess the quality of raw sequencing reads using the FastQC tool; align FASTQ sequencing read files to a reference genome and identify single nucleotide polymorphisms (SNPs); assess the quality of exome sequencing library preparation and also optionally calculate and visualize coverage statistics; analyze exome sequencing data produced by Ion Torrent sequencing machines; merge multiple FASTQ files into a single FASTQ file; read from FASTQ files generated by the Ion Proton, based on the two step alignment method for Ion Proton transcriptome data; other; or any combination of any tool or pipeline discussed herein.

The invention provides systems and methods for creating tools and integrating tools into a pipeline editor. Any suitable method of creating and integrating tools can be used. In some embodiments, a software development kit (SDK) is provided. In certain embodiments, a system of the invention includes a Python SDK. An SDK may be optimized to provide straightforward wrapping, testing, and integration of tools into scalable Apps. The system may include a map-reduce-like framework to allow for parallel processing integration of tools that do not support parallelization natively.

Apps can either be released across the platform or deployed privately for a user group to deploy within their tasks. Custom pipelines can be kept private within a chosen user group.

Systems of the invention can include tools for security and privacy. System 201 can be used to treat data as private and the property of a user or affiliated group. The system can be configured so that even system administrators cannot access data without permission of the owner. In certain embodiments, the security of pipeline editor 101 is provided by a comprehensive encryption and authentication framework, including HTTPS-only web access, SSL-only data transfer, Signed URL data access, Services authentication, TrueCrypt support, and SSL-only services access.

Additionally, systems of the invention can be provided to include reference data. Any suitable genomic data may be stored for use within the system. Examples include: the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, reference data is made available within the context of a database included in the system. Any suitable database structure may be used including relational databases, object-oriented databases, and others. In some embodiments, reference data is stored in a relational database such as a "not-only SQL" (NoSQL) database. In certain embodiments, a graph database is included within systems of the invention.

Using a relational database such as a NoSQL database allows real world information to be modeled with fidelity and allows complexity to be represented.

A graph database such as, for example, Neo4j, can be included to build upon a graph model. Labeled nodes (for informational entities) are connected via directed, typed relationships. Both nodes and relationships may hold arbitrary properties (key-value pairs). There need not be any rigid schema, and node-labels and relationship-types can encode any amount and type of meta-data. Graphs can be imported into and exported out of a graph data base and the relationships depicted in the graph can be treated as records in the database. This allows nodes and the connections between them to be navigated and referenced in real time (i.e., where some prior art many-JOIN SQL-queries in a relational database are associated with an exponential slowdown).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for processing a bioinformatics pipeline, the method comprising:
    receiving, from a user, instructions to process a bioinformatics pipeline, the bioinformatics pipeline comprising a plurality of genomic tools, wherein at least a first one of the genomic tools comprises an executable and wrapper metadata;
    creating a first job for execution, the first job comprising the executable of the first one of the genomic tools and input data, wherein the first job further comprises a cloud instance;
    modifying the bioinformatics pipeline to avoid an error relating to the executable of the first genomic tool, the modification comprising replacing the executable of the first job with an executable of an alternative genomic tool according to the wrapper metadata of the first one of the genomic tools;
    and
    initiating execution of the first job on the cloud instance, wherein the modification of the first job avoids the error.

2. The method of claim 1, further comprising modifying the bioinformatics pipeline to avoid an error that relates to an insufficient resource condition.

3. The method of claim 2, wherein modifying the bioinformatics pipeline to avoid an error related to an insufficient resource condition comprises determining a need for additional resources from the wrapper metadata, and requesting the additional resources for execution of the alternative genomic tool.

4. The method of claim 3, wherein the requested additional resources include sufficient computing power to avoid the insufficient resource condition.

5. The method of claim 4, wherein the requested additional resources include sufficient computer processors to avoid the insufficient resource condition.

6. The method of claim 3, wherein the requested additional resources include sufficient storage space to avoid the insufficient resource condition.

7. The method of claim 1, wherein creating the first job for execution further comprises:
    initiating execution, on a first cloud instance, of the first job; and
    receiving, from the first cloud instance, the error from the executable of the first genomic tool;
    wherein modifying the bioinformatics pipeline is performed in response to receiving the error.

8. The method of claim 1, wherein the executable includes a sequence alignment program and the alternative genomic tool includes an alternative sequence alignment program.

9. The method of claim 1, wherein replacing the executable of the first genomic tool further comprises replacing the first job with a set of jobs.

10. The method of claim 9, wherein replacing the first job with a set of jobs comprises calling for a second one of the tools in the bioinformatics pipeline to generate ancillary data from the input data, the ancillary data to be used as input data by the executable of the alternative genomic tool.

11. The method of claim 3, wherein the requested additional resources include a data file not provided by the user and not included in the input data.

12. The method of claim 1, wherein modifying the bioinformatics pipeline to avoid an error further comprises adding a flag to instructions that send a parameter to the executable of the alternative genomic tool, wherein the parameter controls how the executable of the alternative genomic tool analyzes the input data.

13. The method of claim 1, wherein the wrapper metadata comprises a script that detects an inconsistency.

14. The method of claim 13, wherein the script detects an inconsistency between the executable and input data of the first job.

15. The method of claim 13, wherein the script modifies the bioinformatics pipeline to avoid the error.

16. The method of claim 1, further comprising prompting the user to allow the modification.

17. The method of claim 1, wherein the cloud instance is selected based on the wrapper metadata.

18. A system for processing a bioinformatics pipeline, the system comprising:
- at least one computer hardware processor; and
- at least one non-transitory computer-readable storage medium storing processor-executable instructions that, when executed by the at least one computer hardware processor, cause the at least one computer hardware processor to perform:
  - receiving, from a user, instructions to process a bioinformatics pipeline, the bioinformatics pipeline comprising a plurality of genomic tools, wherein at least a first one of the genomic tools comprises an executable and wrapper metadata;
  - creating a first job for execution, the first job comprising the executable of the first one of the genomic tools and input data, wherein the first job further comprises a cloud instance;
  - modifying the bioinformatics pipeline to avoid an error relating to the executable of the first genomic tool, the modification comprising replacing the executable of the first job with an executable of an alternative genomic tool according to the wrapper metadata of the first one of the genomic tools; and
  - initiating execution of the first job on the cloud instance, wherein the modification of the first job avoids the error.

19. The system of claim 18, wherein modifying the bioinformatics pipeline to avoid an error related to an insufficient resource condition comprises determining a need for additional resources from the wrapper metadata, and requesting the additional resources for execution of the alternative genomic tool.

20. The method of claim 17, wherein the cloud instance is selected based on resource requirements specified in the wrapper metadata.

* * * * *